United States Patent
Weijand et al.

[11] Patent Number: 5,999,857
[45] Date of Patent: Dec. 7, 1999

[54] IMPLANTABLE DEVICE TELEMETRY SYSTEM AND METHOD

[75] Inventors: Koen J. Weijand, Hoensbroek; Richard P. M. Houben, Berg & Terblijt, both of Netherlands; Jeff Wilkinson, Vadnais Heights, Minn.

[73] Assignee: Medtronic, Inc., Minneapolis, Minn.

[21] Appl. No.: 08/768,605

[22] Filed: Dec. 18, 1996

[51] Int. Cl.⁶ .................................................. A61N 1/37
[52] U.S. Cl. ............................................. 607/60; 128/903
[58] Field of Search ...................... 607/32, 60; 128/903

[56] References Cited

U.S. PATENT DOCUMENTS

| | | | |
|---|---|---|---|
| 4,571,589 | 2/1986 | Slocum et al. | 340/870.32 |
| 4,681,111 | 7/1987 | Silvian | 128/419 |
| 4,847,617 | 7/1989 | Silvian | 340/870 |
| 4,944,299 | 7/1990 | Silvian | 128/419 |
| 4,947,407 | 8/1990 | Silvian | 375/94 |
| 4,972,438 | 11/1990 | Silvian | 375/59 |
| 4,980,898 | 12/1990 | Silvian | 375/59 |

*Primary Examiner*—William E. Kamm
*Attorney, Agent, or Firm*—Michael J. Jaro; Harold Patton

[57] ABSTRACT

There is provided an improved telemetry system for use with implantable devices such as cardiac pacemakers and the like, for two-way telemetry between the implanted device and an external programmer. The system employs highly energy efficient oscillators with encoding circuits for synchronous transmission of data symbols, which symbols form the telemetry carrier. The system provides improved circuits for higher density data encoding of sinusoidal symbols, including improved combinations of BPSK, FSK, and ASK encoding. Embodiments of transmitters for both the implanted device and the external programmer, as well as modulator and demodulator circuits, are also disclosed, and specifically include oscillators which switch capacitors between a tank circuit and a recharge path, the switching being controlled to occur at moments of substantially zero coil current, thereby providing high efficiency operation.

7 Claims, 16 Drawing Sheets

IMPLANTABLE DEVICE TELEMETRY SYSTEM AND METHOD

FIELD OF THE INVENTION

The invention relates to implantable medical devices and systems and, more particularly systems and methods for efficiently transmitting information from an implantable device to an external device.

BACKGROUND OF THE INVENTION

For several decades, electronic devices have been implanted in humans and animals. Such devices are generally used to monitor or regulate the functions of body organs and the like. For example, a pacemaker monitors and regulates heart rate, delivering electrical impulses as required to maintain a satisfactory heart beat. Such implantable devices are powered by batteries which have a finite capacity, and which also present a limitation in terms of available peak power. As a result, there is a significant need to minimize the energy expended during operation of the implantable device, and to reduce the peak power required for special situations such as communications with external devices.

In recent years, implantable electronic device technology has rapidly advanced. Sizes and weights have been dramatically decreasing, while functionality has been increasing. These advances have created a corresponding demand for two-way communication between the implanted electronic device and an external device, generally known as a programmer. For example, in a pacemaker system, the programmer downloads data to the implanted pacemaker, such as operating parameters. Thus, an advantage of modern pacemaker systems is that the physician can re-program various operating parameters, such as rate, pulse level, mode, etc. Likewise, the implantable device up-links data to the programmer for analysis, such as patient data (e.g., average heart rate) or device operational data (e.g., battery voltage). Indeed, the pacemaker is capable of storing significant amounts of data for diagnostic purposes, which data frequently must be transmitted to the programmer for evaluation by the physician. Unfortunately, the increasing need for telemetry has resulted in a corresponding increase in demand on implantable device battery power. The telemetry system uses a significant amount of battery power when operational, which affects lifetime. And potentially more important, the telemetry system may greatly increase the current load on the battery during periods of transmission, to the point where battery peak power availability substantially curtails the possible rate of transfer. Many implantable systems, such as pacing systems, can accumulate and store large amounts of event and operational data, and this creates a need to transfer such data reasonably quickly and efficiently. The more the data transfer rate is limited, the longer the physician is tied up. For these and other reasons, efficient transmitter operation is vitally important to the useful life and communications capability of an implantable device.

Well-known transmitter designs presently in use with implantable devices employ the reflected impedance from a resonating LC circuit to transmit data. In such a design, an external coil is inductively coupled with the coil in the LC circuit within the implanted device. LC circuit transmitters are generally very efficient because of the small amounts of current required to transmit the signal relative to other transmission means, such as RF. However, the bandwidth of such systems has been limited. A basic problem of many such transmitters is that the LC tank resonance frequency and the drive frequency are not inherently matched, and are subject to the accuracy of the components. The coils used are often subject to detuning by metal objects, programmer heads, etc.

In addition to the need for improved efficiency transmitters, there is a need to incorporate improved encoding of a form adaptable to the transmitters, and by which higher data rates can be communicated. One form of data encoding that has come into use is BPSK, biphasic shift keying. By this technique, a portion of the carrier referred to as a "symbol," e.g., a fill cycle of a sine wave, is shifted in phase to one of two states, so as to carry a bit of information. Likewise, for FSK, frequency shift keying, a symbol is shifted in frequency; and for ASK, the amplitude of the symbol is shifted from one level to another. However, present circuits for BPSK, FSK or ASK lack the efficiency desired for implantable-type systems, and are generally lacking in terms of providing high data transfer rates.

In view of the importance of telemetric communications with implanted devices such as pacemakers, a telemetry system that extends the battery life of such devices and/or provides increased bandwidth and greater data transfer rates is very desirable. Such a system would enable longer effective lifetimes for implanted devices, as well as a greater communication capability between the implanted devices and the external programmer. Thus, there is a long-felt need for a more efficient telemetry system for use with implantable devices, and specifically for improved transmitters, data encoding techniques, and decoding techniques.

SUMMARY OF THE INVENTION

It is an object of this invention to provide an improved telemetry system and method for an implantable device, incorporating improvements in transmitter design to achieve higher efficiency, improved encoding circuits to enable higher data transfer, and improved receiver demodulator circuitry for receiving and detecting transferred data signals.

Specifically, there are provided energy efficient oscillators for an implantable device telemetry system, which comprise a single high Q coil used as a coupling antenna with zero coil current switching to provide highly efficient operation. Further, the oscillator is combined with encoding circuitry for improved encoding of data into carrier symbols, including combinations of BPSK, ASK and FSK. The transmitter circuitry of this invention provides for synchronization of the encoded data and carrier, by modulating phase, amplitude and/or frequency of successive symbols in the transmitted carrier signal. The symbols are suitably sine wave cycles, but could be one-half sine wave cycle, or plural cycles; the successive cycles from the carrier can also carry the data.

More specifically, there is disclosed an energy efficient oscillator comprising a single coil and dual capacitors that are switched respectively into and out of connection with the coil. In a first embodiment the circuit operates by detecting events of zero current flow through the coil, and switching between the capacitors at moments of zero coil current, whereby each capacitor is recharged near its peak voltage, maximizing efficiency. Thus, during selected instances of zero coil current flow, the capacitor that had been connected to the coil to resonate with it is switched to a power supply, and an alternate capacitor that had been connected to the power supply is switched into a tank circuit with the coil. By this technique, each capacitor is switched when its voltage is at a peak, minimizing the required recharge and thus maximizing efficiency.

In another embodiment, the energy efficient oscillator based on zero coil current control, is modulated by an input data signal to switch among symbols, e.g., one cycle of the sinusoidal carrier signal, wherein each symbol is encoded to simultaneously carry frequency, amplitude and/or phase data. Thus, each symbol is a part of the carrier, having been generated by resonating for a single cycle, plural cycles, or one-half sine wave cycle, before the next symbol is switched into the telemetry stream, at a moment of zero coil current flow. In this way, data is efficiently transmitted by simultaneously modulating each symbol of the carrier with information, so as to provide effectively greater bandwidth and increased data transfer rate. In a specifically disclosed embodiment, symbols are encoded with three different frequencies, two amplitudes and two phases, to transmit about 3.5 data bits per one cycle symbol.

The invention also provides for an improved receiver/demodulator circuit for use in an external programmer of the system of this invention, including circuitry for filtering out VGA monitor noise and a demodulator using a soft receive routine with a DSP for decoding both a clock signal and the data from a received telemetry signal.

There is also disclosed yet another embodiment of a transmitter including both an energy efficient oscillator and encoder for use in an implanted device, which provides the advantages of tank circuit recharging at zero current crossing and synchronous encoding. In yet another specific circuit there is provided an FSK transmitter for use in an external programmer, which provides efficient capacitor switching at zero coil current crossings.

BRIEF DESCRIPTION OF THE DRAWINGS

The foregoing summary, as well as the following detailed description of the preferred embodiment, is better understood when read in conjunction with the appended drawings. While the drawings illustrate preferred embodiments, it is to be understood that the invention is not limited to the specific methods and instrumentalities disclosed.

In the drawings.

DETAILED DESCRIPTION OF PREFERRED EMBODIMENTS

The invention as described in this specification and the figures comprises an overall telemetry system and method, as well as specific preferred system components, e.g., transmitter oscillator, data encoder, and data decoder. The system is characterized by transmission of single symbols which synchronize the data and carrier. Thus, in the preferred circuit embodiments disclosed, the symbol is a single sine wave, although several of the circuits can be adapted to use a half sine wave symbol. Further, the specific circuits of the embodiment disclose techniques for BPSK, ASK and FSK, as well combinations thereof, providing techniques for encoding more data into a symbol. It will be appreciated by those of ordinary skill in the art that the description given herein of the preferred embodiments is exemplary, and does not in any way limit the scope of the invention. For example, applications are used throughout the description wherein the present invention is employed in conjunction with an implantable pacemaker. That example is not intended to limit the invention, as the invention is equally applicable to other devices wherein an efficient transmitter is desirable. While the preferred environment of the invention is a system which includes an implantable device, the invention is also applicable to other environments and system configurations.

Figure 1:
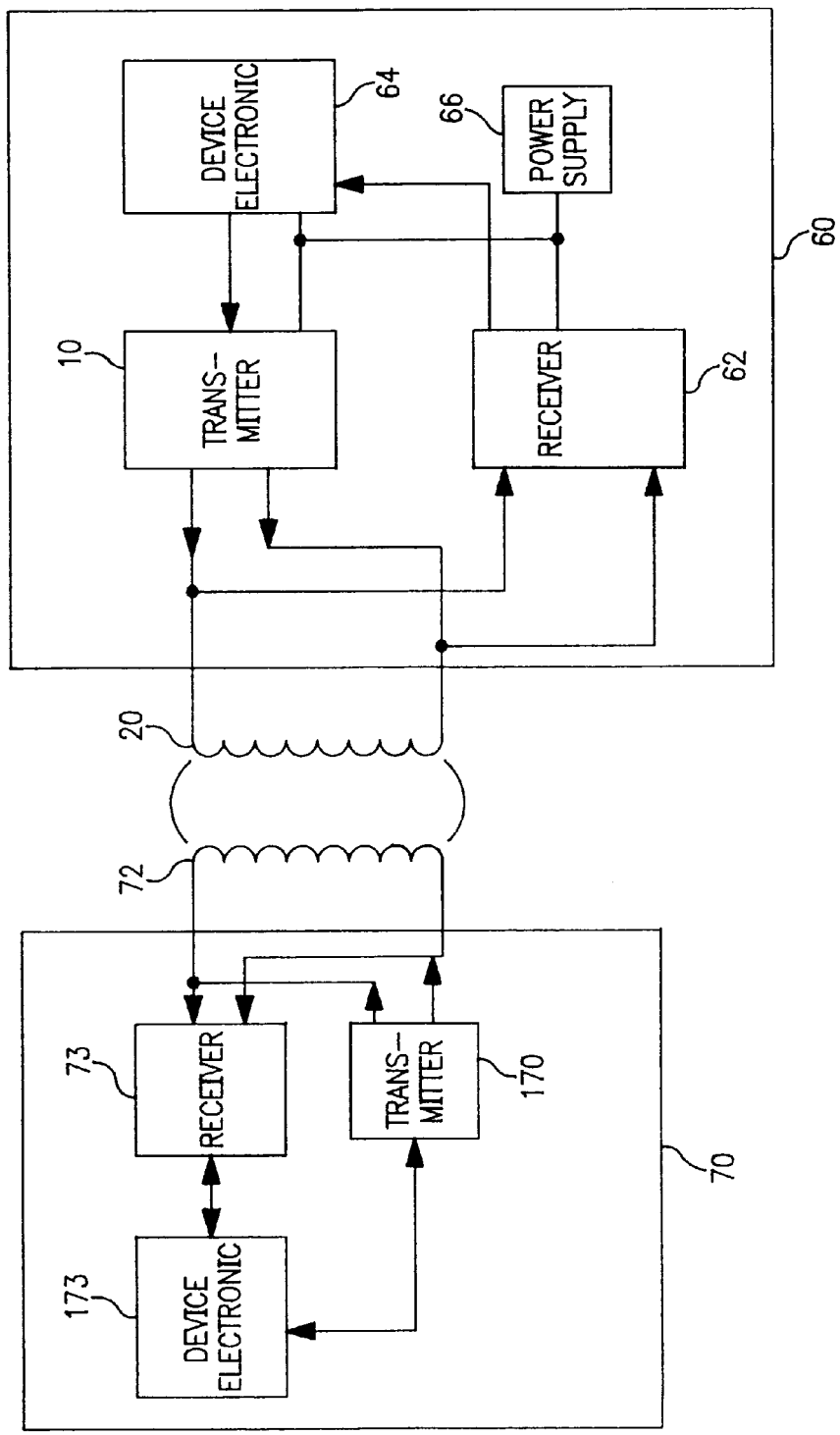
FIG. 1 is a block diagram of the primary components of a representative telemetry system in which the present invention may be employed, having an implanted device in communication with an external device.

Referring to FIG. 1, a block diagram of a implantable device 60 in telemetric communication with an external device 70 (i.e., a programmer) is shown. In such a system, the programmer 70 downloads information to the implantable device 60, and the implantable device 60 up-links information to the programmer 70. The two devices 60 and 70 communicate via an inductive link provided by Q coils 20 and 72. Thus, when the programmer coil 72 is brought into proximity with the implantable device coil 20, a current flow through either coil 20, 72 causes an inductive current in the other coil 72, 20. In an illustrative system, device 60 is an implanted pacemaker, and programmer 70 is adapted in a known manner to be used by a physician to communicate with the pacemaker.

A typical up-link telemetry path begins with a request by the programmer 70 for information from the device 60. In such a case, the device 60 detects and demodulates the request from the programmer 70. The demodulated command then passes to the device electronics 64 as indicated by the arrows. The device electronics 64 retrieves the requested information from memory (not shown separately), and prepares the information for up-link, passing a digital data stream to the transmitter 10. As will be described more fully below, the transmitter 10 uses this digital data to appropriately modulate the current flow through coil 20, which in turn induces a current in coil 72. The receiver 73 in the programmer 70 receives and demodulates the data transmitted from the device 60, completing the telemetry path. Data received in the programmer is processed by the device electronics, shown at 173. During transmission from programmer 70, device electronics controls the encoding of data for transmission from transmitter 170 to the device 60.

Implanted device 60 has a power supply 66, suitably a battery, which provides the power for all of the implantable device circuitry and components. That is, the receiver 62, the device electronics 64 and the transmitter 10 all must share a single power supply 66. As a result, the more frequently the telemetry system is employed, or the less efficient the telemetry system is, the faster the power supply 66 will be depleted. Furthermore, although the system has two-way communication, the bulk of the information flows from the implantable device 60 to the programmer 70. Thus, an energy efficient transmitter 10 will enhance the lifespan of the implantable device 60. Further, with the power supply limitations of a typical implanted device, transmitter efficiency is important in order to provide a good rate of data transmission, which is very important for optimizing the attending doctor's time.

A transmission signal generally comprises two components: A carrier, and data that modulates the carrier. Most often the carrier is an analog signal that is modulated by either analog or digital data. Generally, the carrier signal consumes a substantial portion of the overall transmitter power, e.g., even when no data is present, the carrier may still be present. For this reason, techniques for enhancing the energy efficiency of generating the carrier signal have a significant impact on the efficiency of the transmitter. Thus, the oscillator, which is used to generate the carrier, should be as energy efficient as possible.

Figure 2:
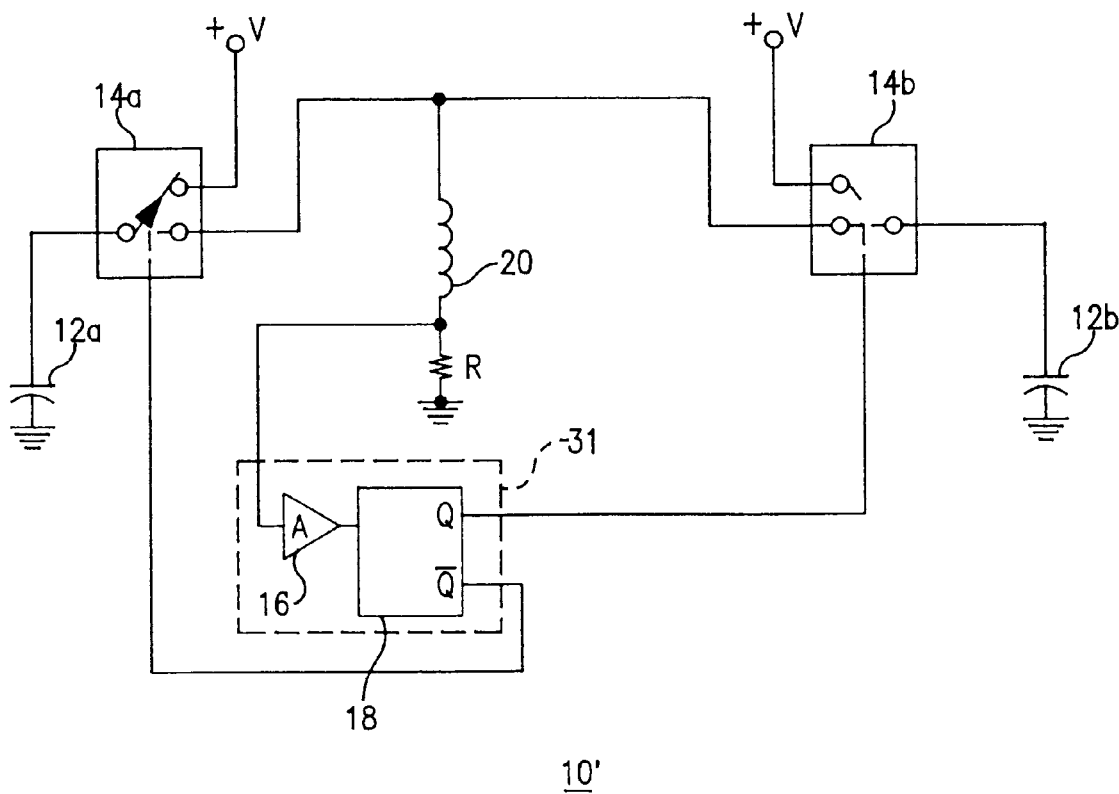
FIG. 2 depicts a first embodiment of an oscillator for use with the present invention.

FIG. 2 depicts a circuit diagram of a preferred embodiment of an oscillator circuit 10' which may be employed to generate the carrier signal of an implantable device transmitter 10. The circuit is characterized by a high Q antenna coil, and switching at zero crossing of the coil current. A single coil 20 is used in combination with two capacitors 12a, 12b. While one capacitor resonates with the coil 20, the other capacitor is connected to the power supply (+V), and recharges. By alternately switching between the two capacitors 12a, 12b, the circuit 10' oscillates. According to an important aspect of the invention, the capacitors are each switched at or near a moment of zero current through the coil 20, at which time the capacitor that had been connected to the coil is near peak voltage. By this technique, the amount of recharge from the power supply to the connected capacitor is minimized.

Figure 3:
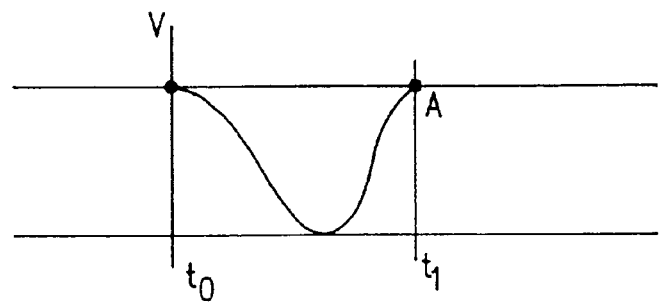
FIG. 3 depicts a single-cycle minimally damped sine wave as a measure of the voltage across a capacitor of the oscillator embodiment of FIG. 2.

As shown in FIG. 2, capacitors 12a and 12b are connected to switches 14a and 14b, respectively. Each switch is configured similarly, with one leg of each switch connected to power source 66 (shown at +V) and the other leg connected to coil 20. As a result of the switch connections, one capacitor is connected to the power source 66 while the other is connected to the coil 20. The circuit 10' can be made to self-oscillate by the addition of control logic 31, which alternately connects the capacitors 12a and 12b to power source 66 and coil 20 via switches 14a and 14b. For example, while switch 14a is connected to the power source 66, switch 14b is connected to the coil 20, and vice-versa. Control logic 31 functions by measuring the current flow through coil 20 and using that current flow to switch the switches 14a, 14b when the current flow is zero. To accomplish this goal, logic 31 converts the voltage sine wave generated across resistance R (which signal represents current through coil 20) into a square wave, and changes states on the leading edge of the square wave. The control logic 31 is comprised of amplifier 16 and flip-flop 18. The signal across R is fed into the amplifier, which is driven to saturation, resulting in a square wave. This square wave output is then fed into a leading edge triggered flip-flop 18, causing the flip-flop outputs Q and Q' to change states each time the current through the coil 20 reaches zero in a positive-going direction. Thus once each cycle the states of Q and Q' are changed, and the switches 14a, 14b change position. In this manner, the respective one of capacitor 12a or 12b that had been connected to coil 20 is disconnected from coil 20 and connected to power source 66, and the other capacitor that had been connected to power source 66 is disconnected from power source 66 and connected to coil 20. In this way, one of capacitors 12a, 12b is allowed to resonate with the coil 20 for a single cycle, while the other capacitor recharges. The voltage across the resonating capacitor is illustrated in FIG. 3, where it is shown that the capacitor only needs to recharge by the small amount Δ.

Several significant efficiencies are gained by switching capacitors 12a, 12b when the current through coil 20 reaches zero. By switching when the current in coil 20 is zero, essentially no power is dissipated from the coil. Moreover, since no current is flowing through the coil at the moment of switching, less noise is generated. Further, when coil 20 has zero current, the capacitor that is connected to it has near peak voltage, such that it only needs to be recharged by the amount of energy lost in a single cycle, which is highly efficient, and generates successive sine wave cycles with smooth, bumpless continuity between successive cycles.

Figure 4:
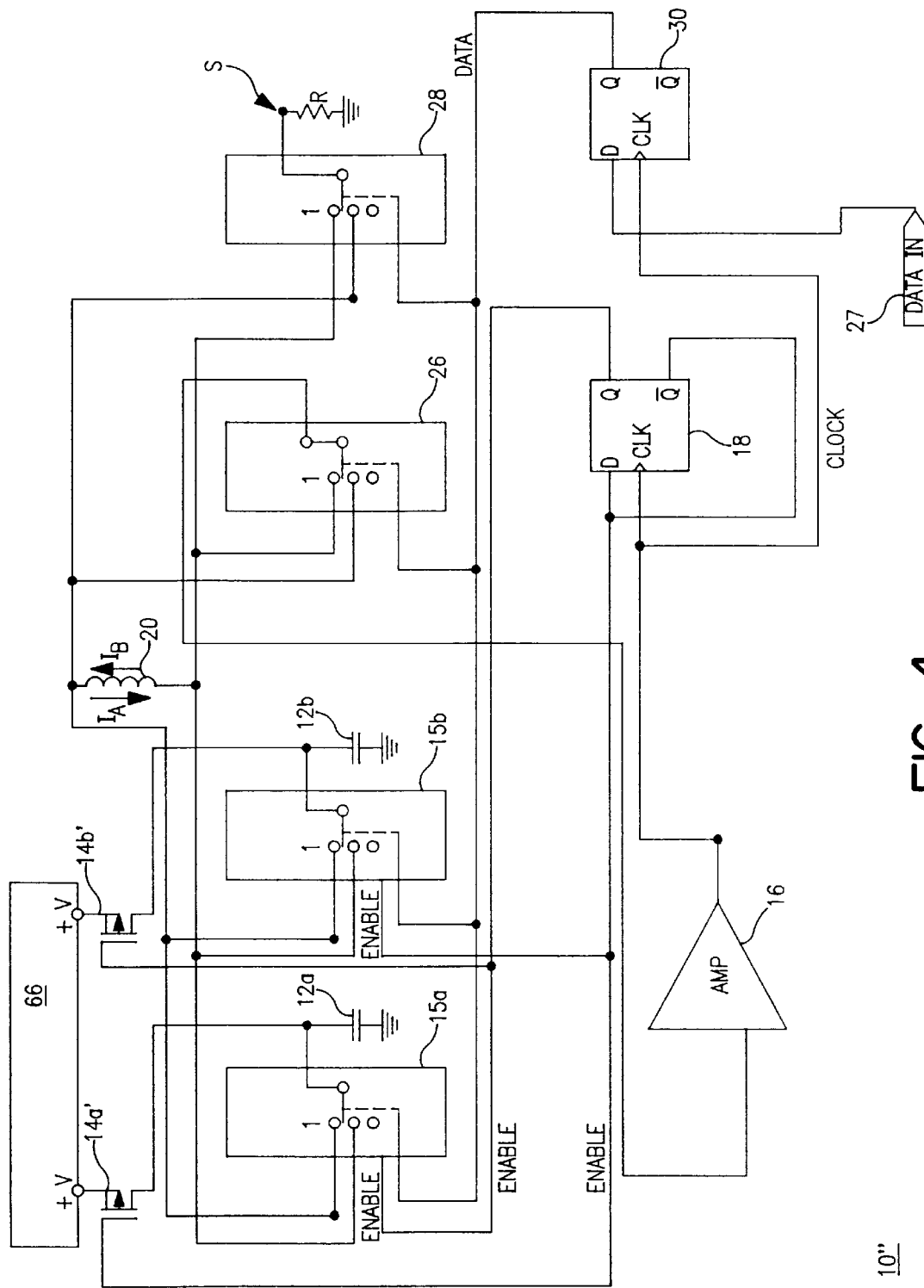
FIG. 4 depicts a transmitter embodiment in the form of a biphasic-shift key (BPSK) transmitter, incorporating aspects of the oscillator depicted in FIG. 2, according to a presently preferred embodiment.

Another advantage of the self-oscillating circuit 10' is that it is easily adapted in accordance with this invention to transmit digital data. Such an adapted circuit is shown in FIG. 4, which presents a diagram of the self-oscillating circuit of FIG. 2 adapted to transmit biphasic shift key (BPSK) data. In this embodiment, BPSK encoding of digital data is effectuated by circuitry that changes the direction of the initial flow of current through the coil 20 in response to a data signal. In other words, the direction of current flow at the start of each cycle, or symbol, can be controlled. Changes in the initial current flow through coil 20 appear to an external receiver as changes in telemetry signal phase, which phase changes can be detected to recover the digital data.

The changes that enable the circuit of FIG. 4 to provide BPSK encoding of a digital data signal are brought about by the addition of switches 15a, 15b, 26 and 28, and additional control logic. As shown, the two capacitors 12a and 12b are connectable to power source 66 by respective FET switches 14a' and 14b'. Capacitor 12a is also connectable to coil 20 by switch 15a, while capacitor 12b is connectable to coil 20 by switch 15a. Switches 26 and 28, along with switches 15a and 15b, control the direction of initial current flow through coil 20. When each switch is in the "0" position, current flows in the $I_B$ direction. By contrast, when each switch is in the "1" position, current flows in the $I_A$ direction. However, each of switches 15a, 15b provides a connection from its corresponding capacitor only when its enable input is high. In a presently preferred embodiment, the switches are implemented using a 3-channel 4053 multiplexer (MUX) chip, with all of the channels tied together and selected. The MUX enable line is used to switch the capacitors into and out of the circuit. Before a capacitor 12a or 12b can connect to the power source 66, an enabling voltage must be applied to the base of the corresponding FET 14' On the other hand, for a capacitor 12a or 12b to connect to the coil 20, an enabling voltage must be applied to the corresponding switch 15a or 15b. During operation of the circuit 10" of FIG. 4, voltage is alternately supplied to one FET 14a, 14b, and then the other. Simultaneously, an enabling voltage is alternately supplied to switches 15a, 15b to permit connection of the appropriate capacitor 12a, 12b to the coil 20. For example, while an enabling voltage is applied to FET 14a, an enabling voltage is applied to the opposing switch 15b to connect capacitor 12b to the coil 20; FET 14b and switch 15a receive no enabling voltage. After the completion of a single resonant cycle, the opposite connections are made.

Similar to the circuit 10' of FIG. 2, the circuit 10" of FIG. 4 also generates a control signal to initiate switching at the moment of zero current through coil 20. To that end, the voltage across a resistor R in series with coil 20 is used to determine the zero current events. Resistor R is connected to coil 20 through switch 28. Those skilled in the art will appreciate that switch 28 may have an internal resistance that be can used in the actual implementation for the current sensing, rather than adding series resistor R. Since the current through resistor R is in phase with the current through coil 20, when the voltage across resistor R as measured at node S is zero, the current through coil 20 is likewise zero. The voltage across resistor R is fed through switches 26 and 28 into amplifier 16, driving it to saturation and thus converting the current sine wave signal into a square wave. The positive-going output of amplifier 16 is used to clock flip-flop 18, which is implemented using a 74HC74 flip-flop. The outputs Q and Q' from flip-flop 18 provide enable signals to control the switching of capacitors 12a and 12b. Specifically, the output Q from flip-flop 18 controls FET 14b' and switch 15a, while the output Q' from flip-flop 18 controls FET 14a' and switch 15b. As a result, each time the current through coil 20 reaches zero in a positive direction, the output from flip-flop 18 changes and capacitors 12a, 12b are switched. This circuit 10" then self-oscillates in the same manner as the circuit 10' of FIG. 2.

In addition to self-oscillating, the circuit 10" encodes a digital data stream from data source 27 into a BPSK telemetry signal output via coil 20. As noted above, the BPSK signal output is effectuated by controlling the direction of current flow through coil 20. Switches 15a, 15b in conjunction with switches 26 and 28 reverse the direction of the initial current flow through the coil 20 in response to data control signals inputted to flip-flop 30. Flip-flop 30, which is implemented using a 74HC74 flip-flop, is in electrical communication with switches 15a, 15b, 26 and 28, providing the switches with control signals that they then translate to a switching configuration that controls the current flow direction. The data in is clocked through flip flop 30 each cycle by the clock signal from amp 16. If a "high" signal (i.e. logic one) is output from flip-flop 30, then each switch 15a, 15b, 26 and 28 will move to the position designated "1" and current will initially flow through coil 20 as indicated by the arrow $I_A$. On the other hand, if the output from flip-flop 30 is a "low" signal, then the switches 15a, 15b, 26 and 28 will move to the position designated "0" and the current will initially flow through coil 20 in the direction indicated by the arrow $I_B$. By this technique, the phase of each sine wave cycle, or of each symbol, is controlled to correspond to the data input.

Figure 5:
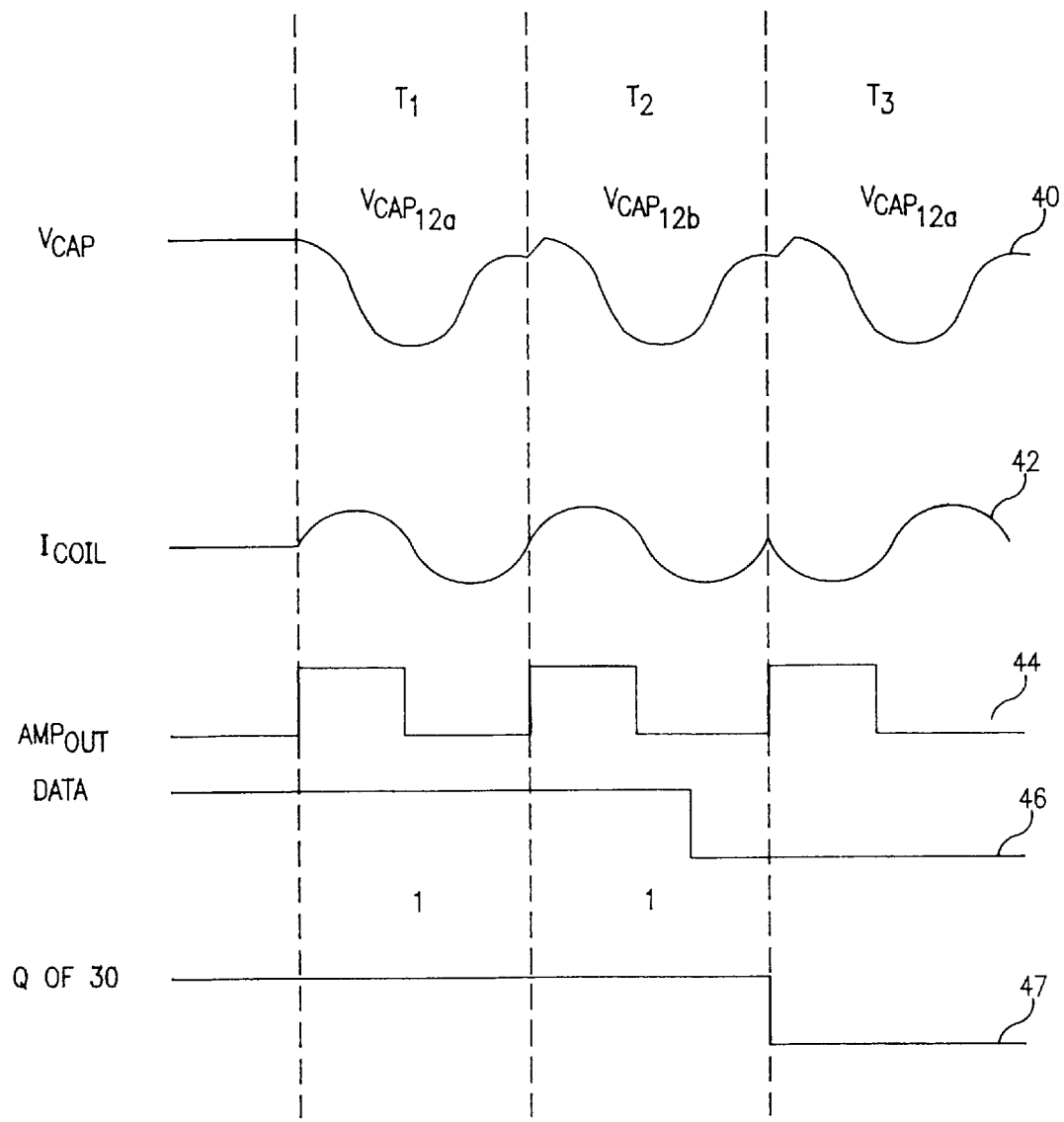
FIG. 5 depicts timing diagrams representative of the operation of the embodiment of FIG. 4.

The function of this preferred embodiment is further illustrated by reference to the timing diagram of FIG. 5. As shown, curve 40 indicates the voltage across capacitors 12a, 12b. The capacitor voltages indicated alternate between capacitors 12a and 12b as they are alternatively switched into and out of series with the coil. The $V_{cap}$ signal for a cycle while the capacitor is in series with the coil is seen to be the same as that of FIG. 3. Curve 42 represents the current through coil 20. Curve 44 represents the output signal from amplifier 16. Curve 46 represents the digital data stream, which modulates the initial direction of current flow through coil 20 at the start of each cycle. Curve 47 represents the output of Q of flip-flop 30, which is the data stream as it is clocked into circuit 10".

When the oscillation begins, the transmitter circuit 10" starts with one capacitor switched to the power source 66 and one capacitor switched to the coil 20. For example, at the start of the T1 cycle, switch 15a is enabled, and FET 14a is disabled. As a result, capacitor 12a resonates for one cycle, causing the current to initially flow through coil 20 in direction $I_A$ since the data signal is at a logic 1. Meanwhile, switch 15b is disabled, and FET 14b is enabled allowing capacitor 12b to fully charge to +V. More generally, at the start of each cycle, the coil current flow direction is determined by the data signal. In the example of data signal 46 shown in FIG. 5, the data signal during time period T1 is a one (1). As a result, switches 15a, 15b, 26 and 28 are set to effect the current flow in the $I_A$ direction. During time period T2, the voltage signal is produced by capacitor 12b, as indicated above. The data signal 46 is again a one (1), resulting in switches 15a, 15b, 26 and 28 remaining set to position "1". Because the data signal has not changed, the direction of current through coil 20 does not change and current signal 42 retains the same phase.

Further illustrating the mechanism of data encoding at about the middle of time period T2 data signal 46 is illustrated as changing to a zero (0). This change in the data causes Q of flip-flop 30 to change state when the next clock pulse 44 arrives at the beginning of time period T3. As a result, switches 15a, 15b, 26 and 28 all change to position "0". The switch change then causes the initial current to flow through coil 20 in a direction $I_B$, as indicated. Note that switch 26 switches to position "0" along with the other switches. For this reason, the signal to the amplifier 16 is not phase shifted, allowing the square wave output of the amplifier 16 to maintain a constant clock signal. Accordingly, the transmitter circuit 10" produces a BPSK signal across coil 20. When coil 20 is brought into proximity of a receiving coil (e.g., coil 72 in FIG. 1) the BPSK signal will be reproduced in the receiver, and the data stream can be decoded. This embodiment is thus characterized by the generation of data symbols which, in fact, also constitute the carrier. Although the symbol has been illustrated as a full sine wave, the circuit of FIG. 4 can be adapted to produce ½ cycle symbols, or n cycle symbols.

Figure 6:
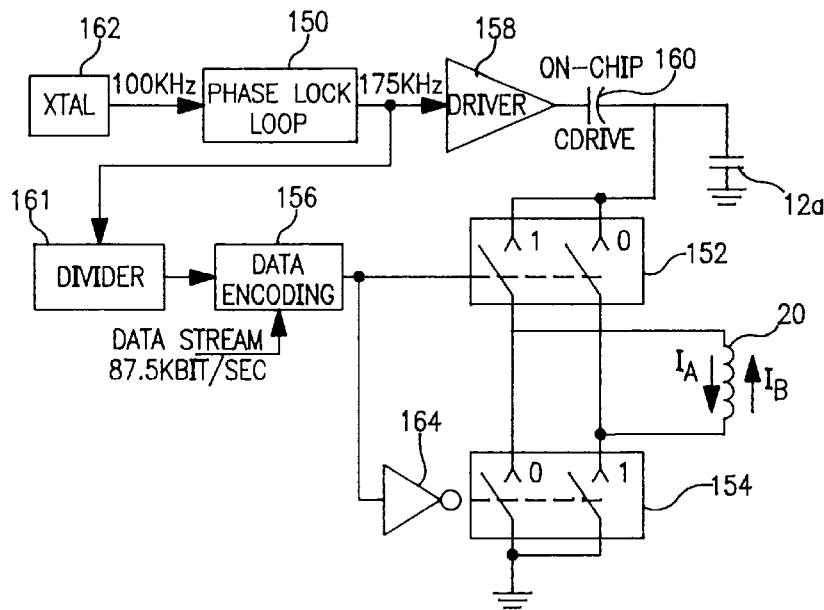
FIG. 6 depicts another embodiment of a BPSK transmitter using the principles of zero current current switching.
Figure 7:
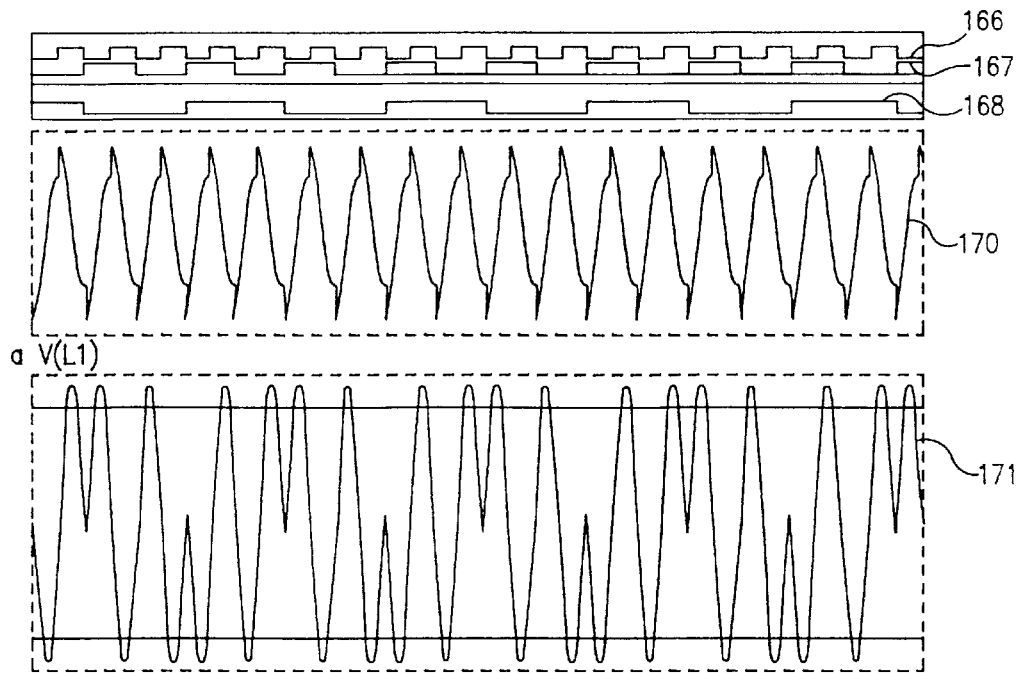
FIG. 7 depicts a timing diagram of the operation of the embodiment of FIG. 6.

The transmitter circuit of FIG. 4 has the advantages of switching at moments of zero coil current flow, thereby producing data encoded symbols which are synchronized with the start of each carrier cycle. Another transmitter embodiment which provides substantially synchronous operation, is illustrated by FIGS. 6 and 7. In this circuit, there is no zero coil current sensing, but switching occurs very close to zero coil current crossings, such that there is very little symbol length error. FIG. 6 presents an embodiment of a BPSK transmitter that switches the current through an antenna coil 20 at a moment very close to zero coil current and cyclically recharges a single resonating capacitor 12a. As with the previous embodiment (i.e., circuit 10"), the circuit embodiment of FIG. 6 operates generally on the principle of a tank circuit, but also employs a drive circuit operating at the resonant frequency of the tank circuit. When the circuit is configured appropriately, as is described more fully below, capacitor 12a and antenna coil 20 function as a tank circuit tuned to the desired resonant frequency, e.g., 175 kHz, with the driver circuit also generating a 175 kHz signal.

A significant aspect of this embodiment is that the circuit generates two separate, closely-matched frequencies during operation. One of those frequencies is generated by the tank circuit, and the other is generated by crystal 162 in conjunction with phase-locked loop 150 (PLL). The tank circuit frequency, as described in further detail below, is used to generate the carrier frequency for the transmitter, suitably 175 kHz; the crystal derived frequency, also 175 kHz, is used to clock the digital data signal and to periodically recharge the capacitor 12a.

Turning now to the details of the circuit, crystal 162 provides an accurate and stable 100 kHz time base for the circuit. A PLL 150 is used to derive a 175 kHz square wave according to well-known techniques. The PLL output signal is then used in two separate ways: First, the output signal is used to generate as a clock signal; and second, the output signal is used to recharge capacitor 122 at each peak of the capacitor voltage signal.

In its first function, providing a clock, the PLL 150 delivers the 175 kHz signal to divider 161. Divider 161 divides the clock signal by two (2), deriving a 87.5 kHz signal. That 87.5 kHz signal is then used to clock data encoder 156. In this exemplary, each data bit to be transmitted utilizes two cycles of the carrier frequency, and thus a 87.5 kHz clock signal is required. Stated another way, each symbol is two sine wave cycles. Data encoder 156, inverter 164 and switches 152 and 154 provide the necessary logic to control the phase encoding by changing the direction of current flow through coil 20 at appropriate times, as determined by the clock signal.

In its second function, providing a capacitor recharge signal, the PLL 150 output is inputted to driver 158, which provides recharge pulses to capacitor 12a. The driver output is coupled to capacitor 160, which is in series with tank capacitor 12a. These two capacitors provide a capacitive divider, enabling control of the power level of the recharge pulses delivered to capacitor 12a. For example, capacitor 160 can be tuned to give about a one-tenth, or a 10% recharge pulse to capacitor 12a, which is important in achieving maximum efficiency in the recharge operation.

When the circuit is operational, capacitor 12a is connected in series with coil 20 resonate. This connection is made via switches 152 and 154, which are connected in one of two positions ("0" or "1") determined by the data signal via encoder 156. For either position, capacitor 12a and coil 20 resonant. As with any resonant circuit, a damped sine wave results, and here the capacitor is recharged each cycle, as described above. It is to be noted that while there can be some drift between the tank circuit signal and the driver recharge signal, the effect on the output is minimal, such that there is little modulation of the symbol length. Further, a small variation in symbol length is not a problem, since the data encoding is synchronized to the capacitor recharge pulses; since the capacitor is recharged at times of switching, the recharge occurs substantially at zero coil current and maximum capacitor voltage.

As previously stated, capacitor 12a and coil 20 are connected via switches 152 and 154. Moreover, those switches are in electrical communication with data encoder 156. When the data encoder 156 outputs a high signal, corresponding to a data one, switches 152 and 154 move to the position designated "1" as shown in FIG. 6. As a result, coil 20 is connected to capacitor 12a such that the initial direction of current flow through the coil 20 is in the direction $I_A$. On the other hand, when data encoder 156 outputs a low signal, corresponding to a data zero, switch 152 and 154 move to the position designated "0". As a result, the coil is connected to capacitor 12a such that the initial current flow through the coil 20 is in a direction $I_B$. Inverter 164 is electrically coupled between data encoder 156 and switch 154, as switch 154 requires the inverse of the logical signal provided to switch 152. In this manner, phase shift encoding, or BPSK is provided, with each symbol being two cycles.

Further details of the operation of the transmitter of FIG. 6 can be understood by referring to the timing diagrams presented in FIG. 7. The output from PLL 150 is graphically depicted by curve 166. This represents the 175 kHz clock signal that is used to charge capacitor 12a, in addition to providing the base frequency to divider 161, the output of which is shown at 167. The data signal from encoder 156 is shown at 168. Curve 170 graphically depicts the voltage measured across capacitor 12a, illustrating the charge and discharge cycles experienced by the capacitor 12a. In this example, the data signal represents alternating ones and zeros for simplicity. As shown at 171, the current through coil 20 changes phase at each change in state of the encoded data signal. The change in phase is effectuated by changing the states of switches 152 and 154, causing a corresponding change in the direction of current flow through coil 20.

In addition to the BPSK systems described above, FSK (Frequency Shift Keying) and ASK (Amplitude Shift Keying) encoding can also be used to further increase the bandwidth of the system. Reference is made to FIGS. 8, 8A–8F, and 9, which illustrate a combined ASK and FSK transmitter circuit 11. The circuit employs two capacitors, power source 66 and a series of multiplexer switches 32a, 32b, 36, 34a and 34b, together with an inductor 20 (i.e., the antenna coil). Switches 32a, 32b and 34b are set to a 0 or 1 position by a logic 0 or 1 respectively; switch 34a is set to a 0 or 1 position by data signal C only when the enable signal D is a logic 1. As will be described more fully below, by sending the appropriate control signals A, B and C to the illustrated switches, as well as an enable signal D to switch 34a, the ASK/FSK circuit 11 of FIG. 8 selects between one of six possible states. Each state comprises one of three (3) frequencies $f_1$, $f_2$ and $f_3$, and one of two (2) amplitudes, $A_1$ and $A_2$. Additionally, as is seen below in connection with FIG. 10, by combining the FSK/ASK circuit 11 with BPSK encoder of the type shown in FIG. 4, a total of twelve possible sinusoidal symbols can be generated and transmitted. Twelve symbols corresponds to roughly three and one-half bits of data per symbol. That is, by assigning a binary number to each of the twelve symbols (e.g., Symbol S1=0000; S2=0001; S3=0010, ... S12=1100) approximately three and one-half bits of data can be transmitted with each symbol. Thus, for example, if a 175 kHz carrier frequency is used, up to 600 k bits per second can be transmitted.

Figure 8:
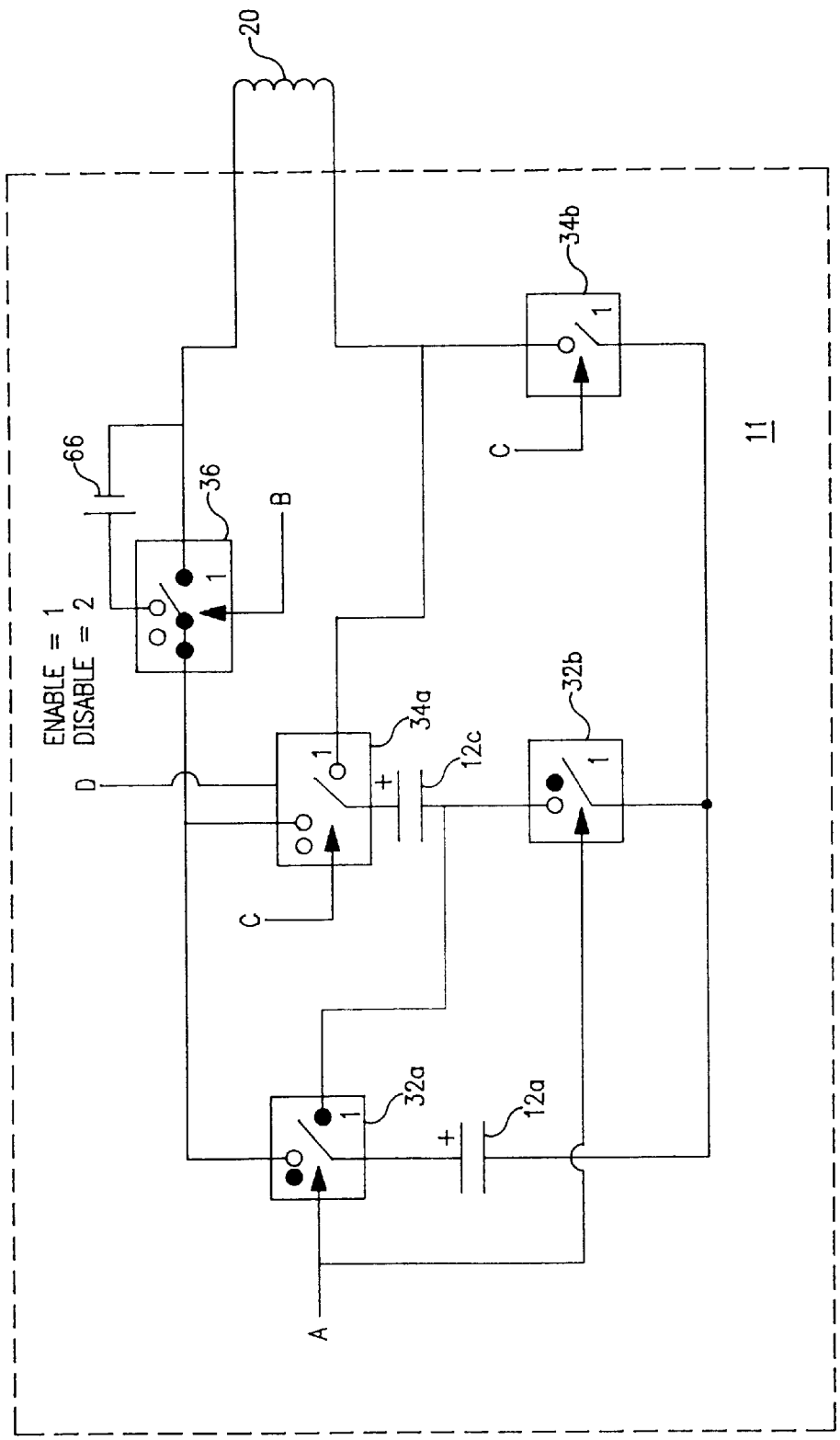
FIG. 8 is a schematic diagram of an ASK/FSK encoding portion of a transmitter circuit according to an aspect of the present invention.

The operation of the ASK/FSK circuit 11 depicted in FIG. 8 can be better understood in conjunction with the simplified circuit diagrams of FIGS. 8A–F. Each simplified circuit corresponds to one of the six states selectable via control signals A, B, C and D, provided from a data input. Appropriately setting the control signals A, B, C and D converts the ASK/FSK circuit 11 into one of the simplified resonant circuits depicted in FIGS. 8A–F. In the preferred embodiment, the capacitors 12a and 12c are selected to have equal values. As a result, the resonant frequency of each of the equivalent circuits 8A–F is related to the frequency:

$$F = \frac{1}{2\pi} \frac{1}{\sqrt{LC}}$$

Where:

L is the value in Henries of the antenna coil 20; and,

C is the capacitance 12a or 12c in Farads.

Using the two equal capacitors 12a and 12c, three different resonant frequencies can be obtained. The first frequency derived is that of the single capacitor circuits depicted in FIGS. 8A and 8B, each of which has a resonant frequency equal to F. The second resonant frequency is obtained by combining the two capacitors 12a and 12c in parallel as depicted in the circuits of FIGS. 8C and 8D. As a result, the two circuits of FIG. 8C and 8D each have a resonant frequency of $(1/\sqrt{2})*F$. The third resonant frequency is obtained by combining the capacitors 12a and 12c in a series configuration, as depicted in the equivalent circuits of FIGS. 8E and 8F. The resulting resonant frequency of the series capacitor circuits is $\sqrt{2}*F$.

The number of states available in the ASK/FSK circuit 11 is doubled to six by adding the voltage of power source 66 into the resonant circuits. By this means, the sinusoidal output signal from ASK/FSK circuit 11 can be switched between one of two amplitude values (A and 2A). When combined with the 3 frequencies (i.e., F, $\sqrt{2}*F$ and $(1/\sqrt{2})*F$), the two amplitudes bring the combined number of states available to six. When those six states are combined with biphasic switching as in the circuit of FIG. 4, the total number of states available comes to twelve.

Table 1, below, provides a convenient cross reference of control signal settings and the corresponding simplified circuit configurations that result from those settings.

TABLE 1

Figure 8A:
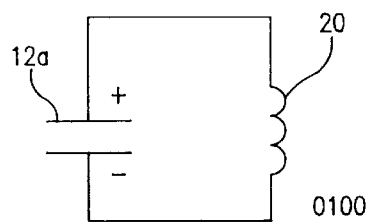
FIGS. 8A–F are schematics of respective simplified circuits derived from the ASK/FSK circuit of FIG. 8 corresponding to selected control signals.
Figure 8B:
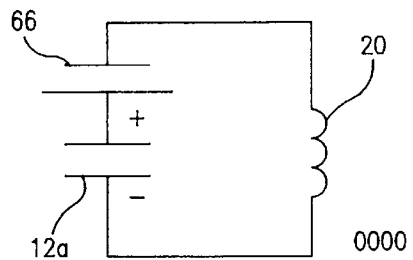
Figure 8C:
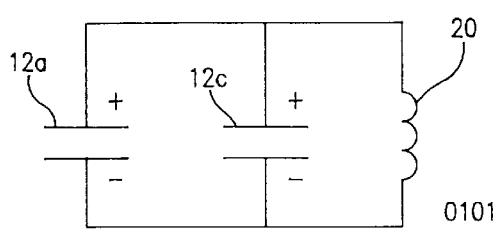
Figure 8D:
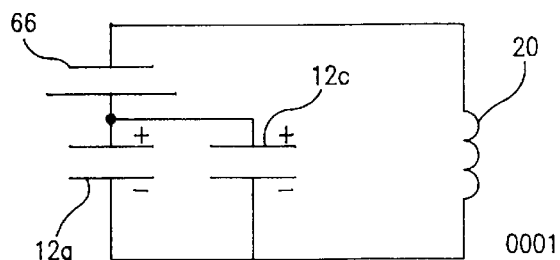
Figure 8E:
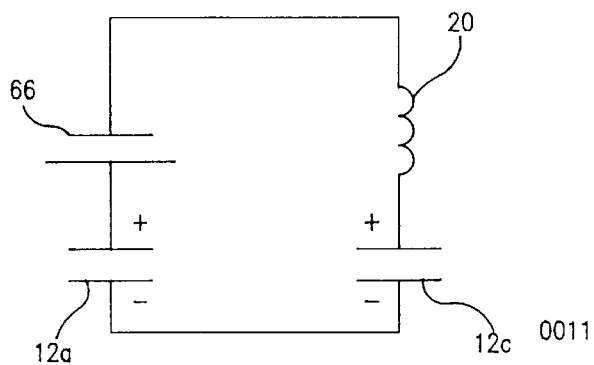
Figure 8F:
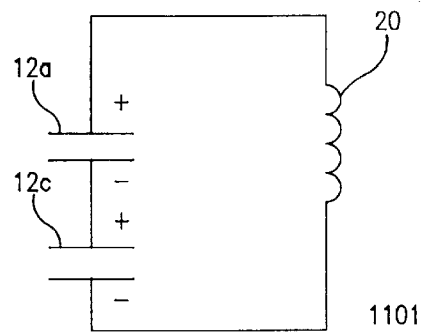

| Control Signal Function | | | | |
|---|---|---|---|---|
| Control Signals | | | | Resulting |
| A | B | C | D | Circuit |
| 0 | 1 | 0 | 0 | Figure 8A |
| 0 | 0 | 0 | 0 | Figure 8B |
| 0 | 1 | 0 | 1 | Figure 8C |
| 0 | 0 | 0 | 1 | Figure 8D |
| 0 | 0 | 1 | 1 | Figure 8E |
| 1 | 1 | 0 | 1 | Figure 8F |

For the data word 0100, capacitor 12a is simply in series with coil 20, as seen in FIG. 8A. For data word 0000, power source 66 is placed in series, giving the circuit of FIG. 8B. When control signal D is a logic 1, switch 34a is enabled; thus, for data word 0101, capacitor 12c is placed in parallel with capacitor 12a, and the circuit of FIG. 8C results. For data word 0101, switc 36 places power source 66 in the circuit, yielding FIG. 8D. When signal C is at logic 1, the two capacitors are placed in series, yielding the equivalent circuits of FIGS. 8E and 8F. It is to be understood that FIG. 8 illustrates the manner of encoding so as to generate symbols representative of the data input; in order to be functional, the circuit is modified in accordance with the principles of FIG. 4, to provide back and forth switching between the pair of capacitors which are connected to the coil, and a like pair of capacitors which are being recharged.

Figure 9:
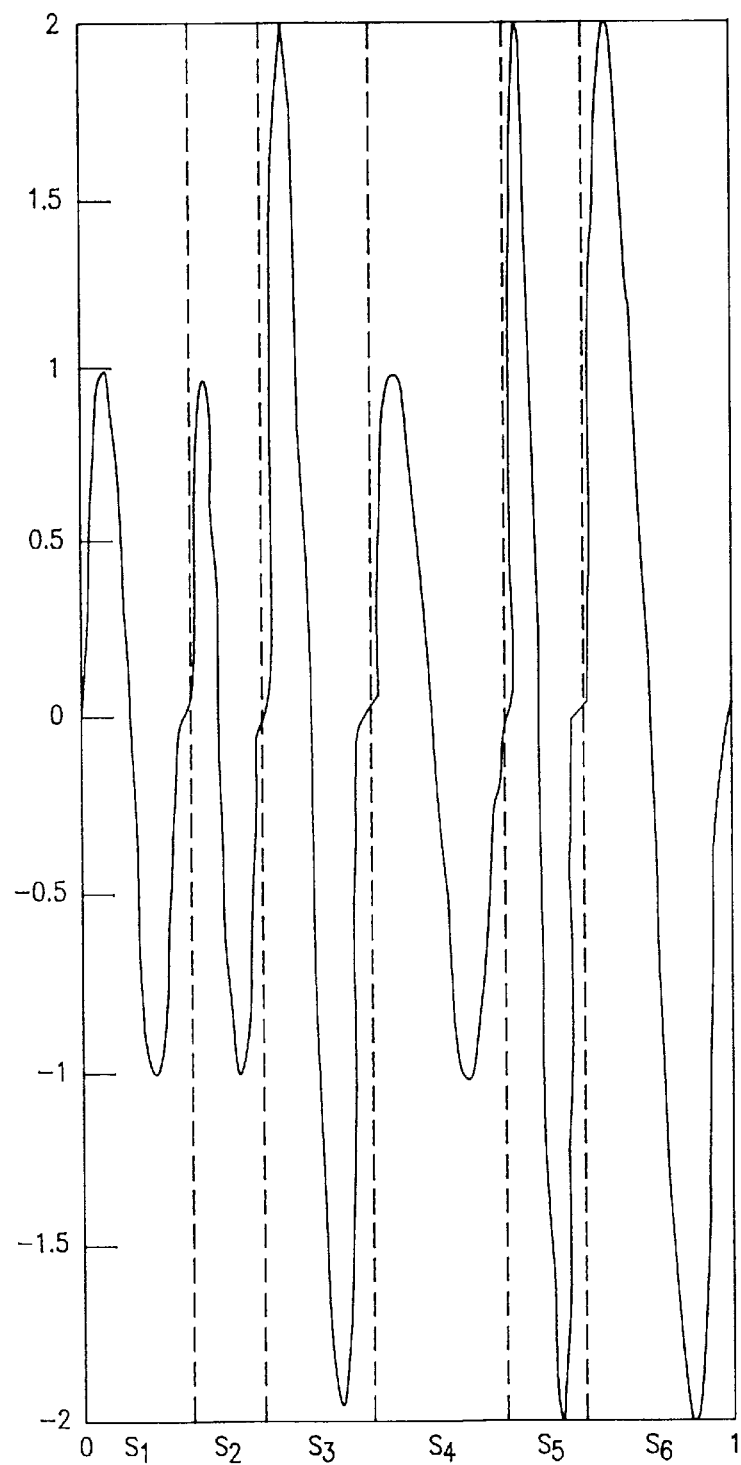
FIG. 9 graphically depicts the sinusoidal symbols produced by the ASK/FSK transmitter circuit of FIG. 8.

FIG. 9 presents the resulting sinusoidal symbols that correspond to the simplified circuits of FIGS. 8A–F. Table 2 below provides a convenient cross reference of symbols and simplified circuits.

TABLE 2

| Symbol - Circuit Cross Reference | | |
|---|---|---|
| Symbol | Figure | Frequency |
| S1 | 8A | F |
| S2 | 8E | $\sqrt{2}*F$ |
| S3 | 8B | F |
| s4 | 8C | $(1/\sqrt{2})*F$ |
| S5 | 8F | $\sqrt{2}*F$ |
| S6 | 8D | $(1/\sqrt{2})*F$ |

As indicated by FIG. 9 and TABLE 2, each simplified circuit produces a unique sinusoidal symbol, which for this ASK/FSK illustration can be a selected one of six different configurations.

Figure 10:
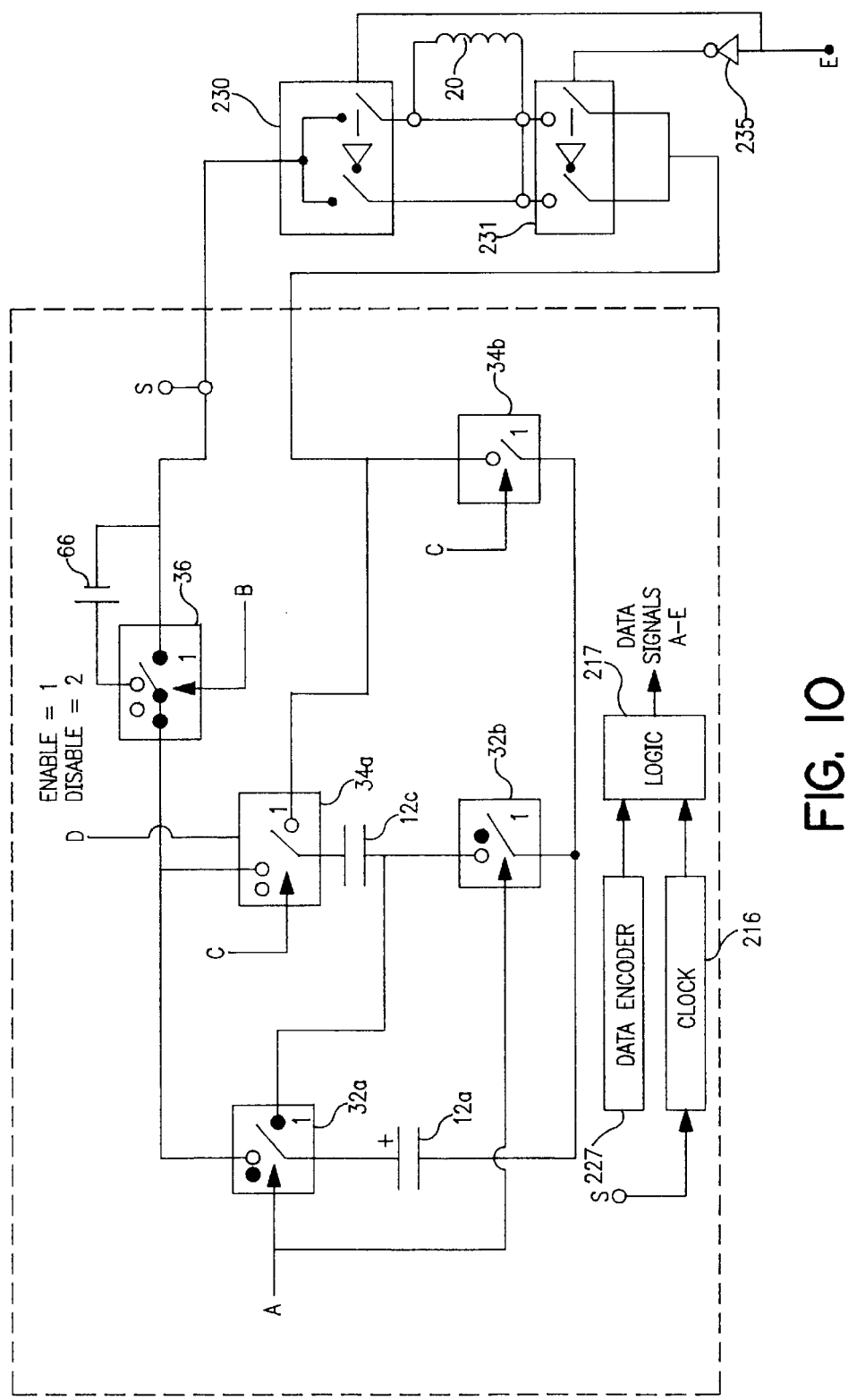
FIG. 10 is a schematic diagram of a transmitter encoding circuit incorporating ASK, FSK and BPSK encoding according to the present invention.

FIG. 10 shows the ASK/FSK circuit 11 (of FIG. 8) integrated into the BPSK transmitter 10″ first described with reference to FIG. 4. The circuit of FIG. 8 is modified by adding switching to control initial current direction, and thus phase, thereby adding BPSK. In circuit 21 of FIG. 10, switches 230 and 231 are added. Switch 230 is controlled by control signal E; switch 231 is controlled by the E signal after passing through inverter 235. Thus, when E is a logic 1, the current flows in a first direction through coil 20; when it is logic 0, the current direction is reversed. Data signals A–E are provided from data encoder 227, clock circuit 216, and logic 217, in the same manner as illustrated in FIG. 4; clock signals are likewise derived from zero crossings of the coil current signal, which signal is taken at point S. It is to be understood that additional circuitry (not shown) is included to provide capacitor recharge, as in the circuit of FIG. 4. For example, two circuits 11 as shown in FIG. 8 can be connected alternately into the circuit of FIG. 10, and to the battery for recharge.

Figure 11:
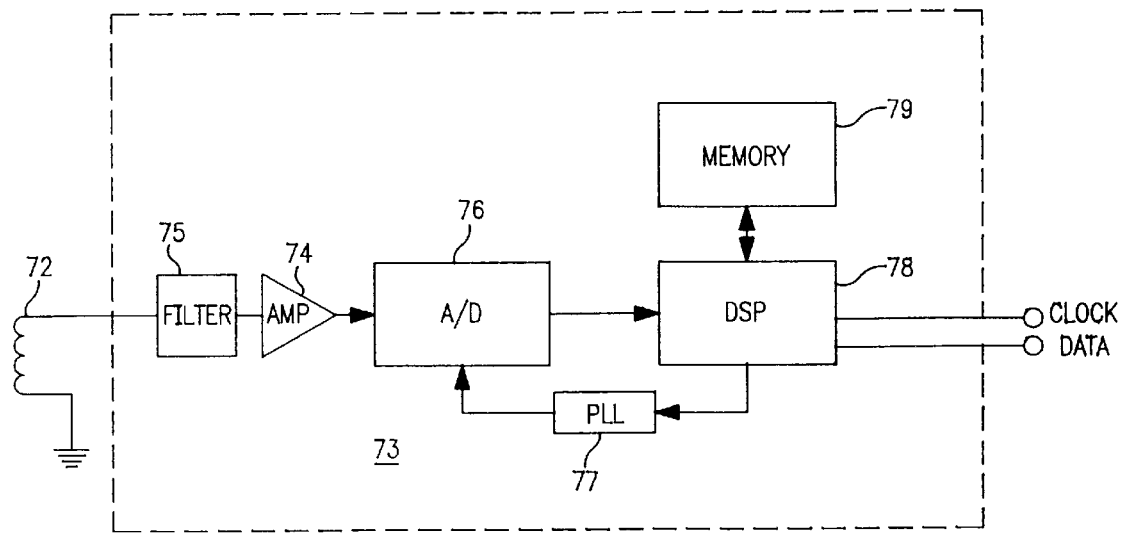
FIG. 11 is a schematic diagram of a receiver/demodulator for use in the external programmer of the system of this invention.

Attention is now shifted to the receiver 73 of the external programmer 70 as shown in FIG. 1. FIG. 11 depicts a preferred embodiment of a receiver 73 that receives and decodes the telemetry signal received from the implantable device transmitter 10. For simplicity and brevity, the decoder techniques are described in the context of a BPSK telemetry signal; however, those skilled in the art will appreciate that the principles described herein for decoding a BPSK signal are equally applicable to FSK and ASK signals after appropriate modifications. As seen in FIG. 11, the receiving coil 72 is connected to a band-pass filter 75, which eliminates noise and extraneous signals from the incoming telemetry signal. The output of band-pass filter 75 is connected to amplifier 74, which amplifies the filtered telemetry signal in preparation for analog-to-digital conversion. The output of amplifier 74 feeds A/D converter 76, which converts the analog telemetry signal into a sampled digital signal. The A/D converter 76 output is, in turn, coupled to a digital signal processor (DSP) 78, which operates on the digital signal to recover the clock and data from the telemetry signal. A phase-locked loop 77 is connected between A/D converter 76 and DSP 78 to adjust the sampling rate of A/D converter 77. Additionally, memory 79, which may comprise any combination of well-known storage devices such as ROM, RAM, EEPROM and the like, is coupled to DSP 78 to provide software program and data storage space. As will be described more fully below, the DSP 78 executes a software program which is stored in and executes from memory 79, that processes the sampled signal.

Figure 12:
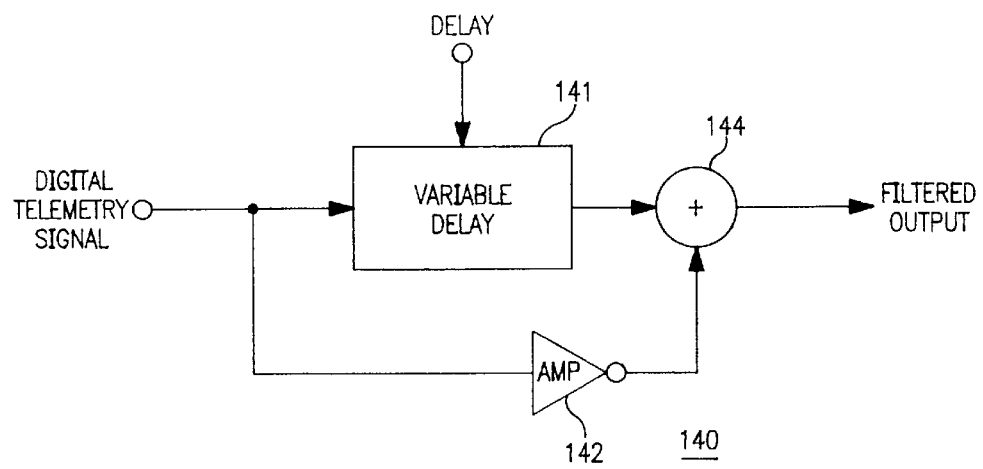
FIG. 12 is an operational block diagram of a VGA monitor noise digital filter as used in an external programmer of the system of this invention.

An incoming analog telemetry signal is converted to a set of samples that are processed by the DSP 78 to recover the data and clock information transmitted by the implanted device 60. However, during the transmission of the telemetry signal from the implanted device 60 to the programmer, the telemetry signal typically experiences noise. VGA monitors, for example, are known to be primary noise contributors. Accordingly an aspect of the present invention is the application of a digital filter having a comb-shaped frequency response to the digital data points. Such a filter removes the VGA monitor induced noise while leaving the original telemetry signal unaltered. FIG. 12 presents a functional block diagram of a digital filter 140 that provides such as a comb-shaped frequency response. As shown, the digital telemetry signal is fed to a variable delay 141, which provides a programmable delay, and also to an inverter 142. The outputs of the variable delay 140 and inverter 142 are summed by adder function 144. Specifically, the variable delay is selected as a function of the fundamental frequency of a VGA monitor scan rate, i.e., 34 kHz. Thus, the variable delay is set to $1/34000$ or approximately $30\mu$ seconds. The resulting filter suppresses the fundamental and harmonic frequencies of noise generated by a VGA monitor, by effectively subtracting out the noise. This operation is particularly important for a telemetry system in a pacing environment, or for other implantable systems.

Figure 13:
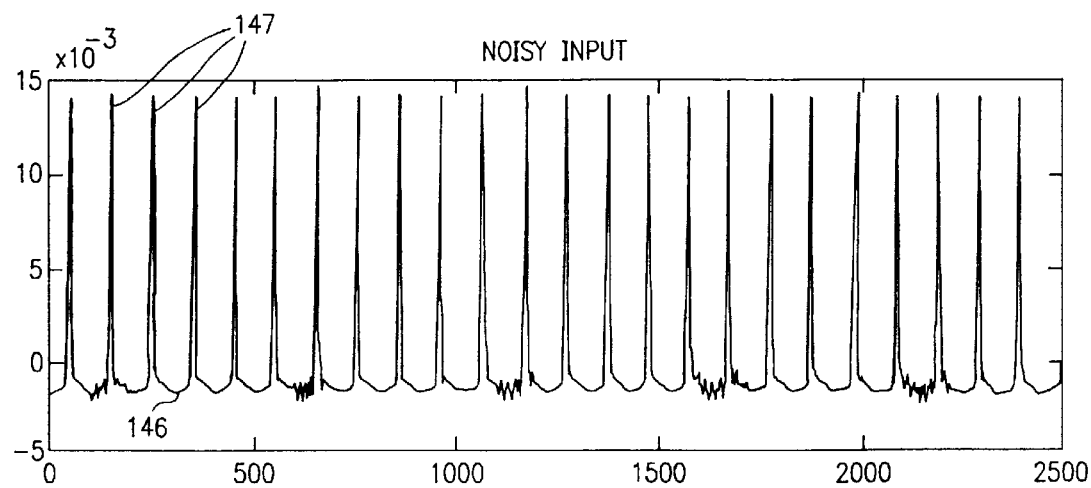
FIG. 13 depicts a telemetry signal containing VGA monitor noise spikes.
Figure 14:
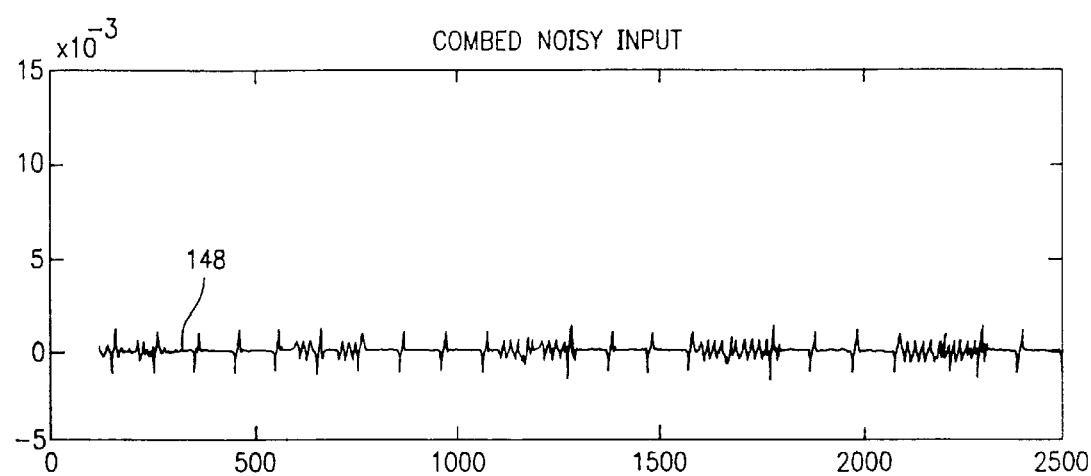
FIG. 14 depicts a telemetry signal after the effective removal of VGA. monitor noise by the digital filter of FIG. 12.

FIGS. 13 and 14 further illustrate the operation of the digital filter 140. FIG. 13 graphically depicts an exemplary telemetry signal having noise spikes 147, which are presumed to have been introduced by a VGA monitor (not shown). As a result of noise spikes 147, the telemetry signal is barely visible. By contrast, FIG. 14 presents the same exemplary signal as in FIG. 13, but after it has been processed through digital filter 140. Notably, as depicted in FIG. 14, the noise spikes 147 have been effectively removed, while the telemetry signal remains intact.

Figure 15:
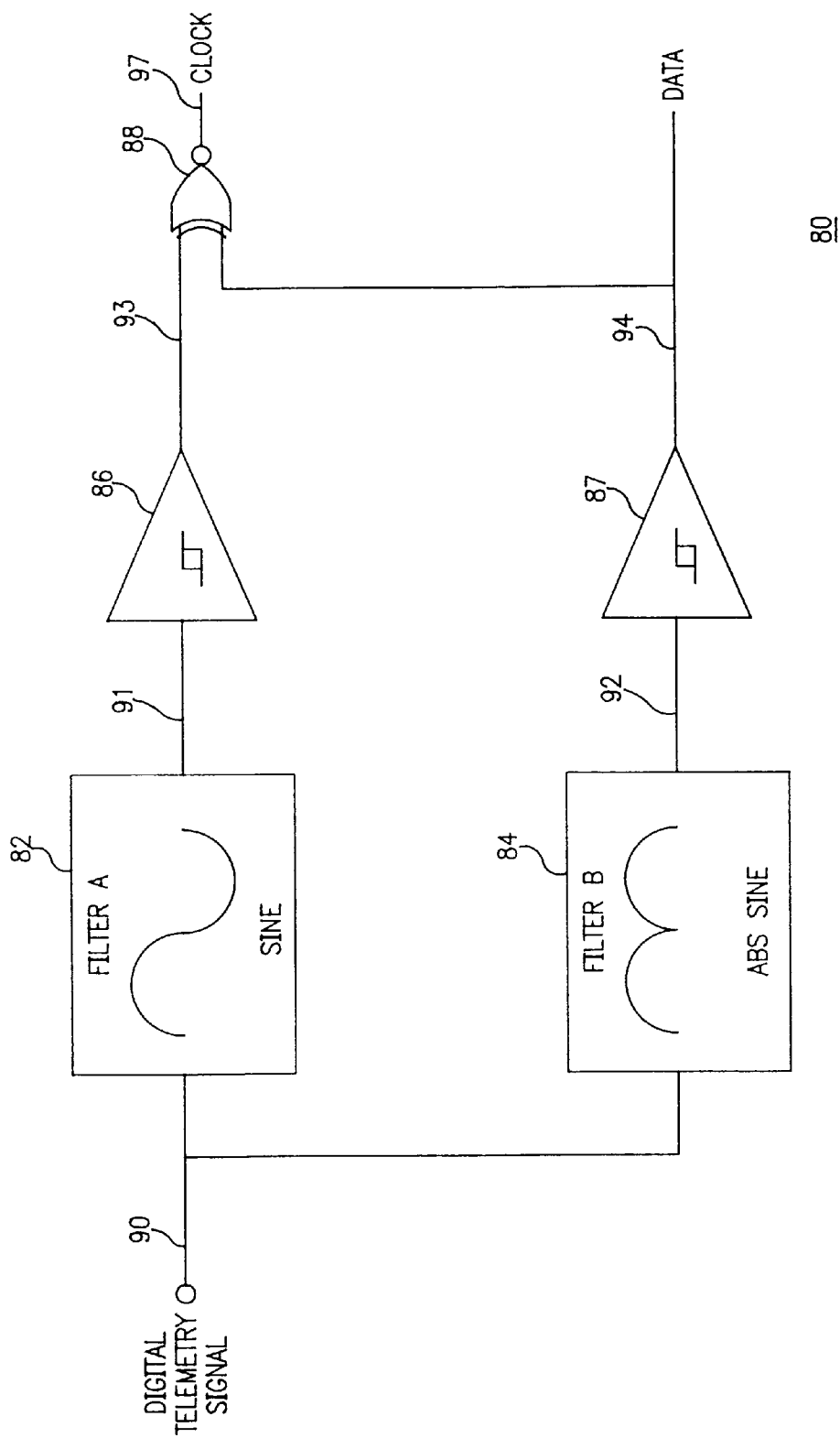
FIG. 15 is a functional block diagram of a soft receive program for demodulating signals received from the implanted device.

After the digital telemetry signal has been filtered for VGA monitor induced noise, it is ready to be demodulated. According to an aspect of the present invention, a software program executing on DSP 78 (hereinafter the soft receiver program) demodulates the digital telemetry signal. Referring to FIG. 15, a functional block diagram of the presently preferred soft receiver program 80 is presented. Essentially, the soft receiver program uses a correlation based technique to convert the sampled signal input into respective clock and data outputs. To accomplish this, the soft receiver 80 comprises a first digital filter (Filter A) 82, which correlates the digital data with coefficients representing a sine wave of the same frequency, and a second digital filter (Filter B) 84, which correlates the digital data with coefficients representing an absolute sine wave, as illustrated. Preferably, both digital filters are implemented as finite impulse response (FIR) digital filters. The output of each filter 82, 84 is coupled to a corresponding level detection function 86,87. As is described more fully below, the outputs 93, 94 of the level detection functions 86, 87 are coupled to an exclusive-or function 88, which reproduces the clock signal. The direct output of level detector 87 produces the data signal.

Figure 16:
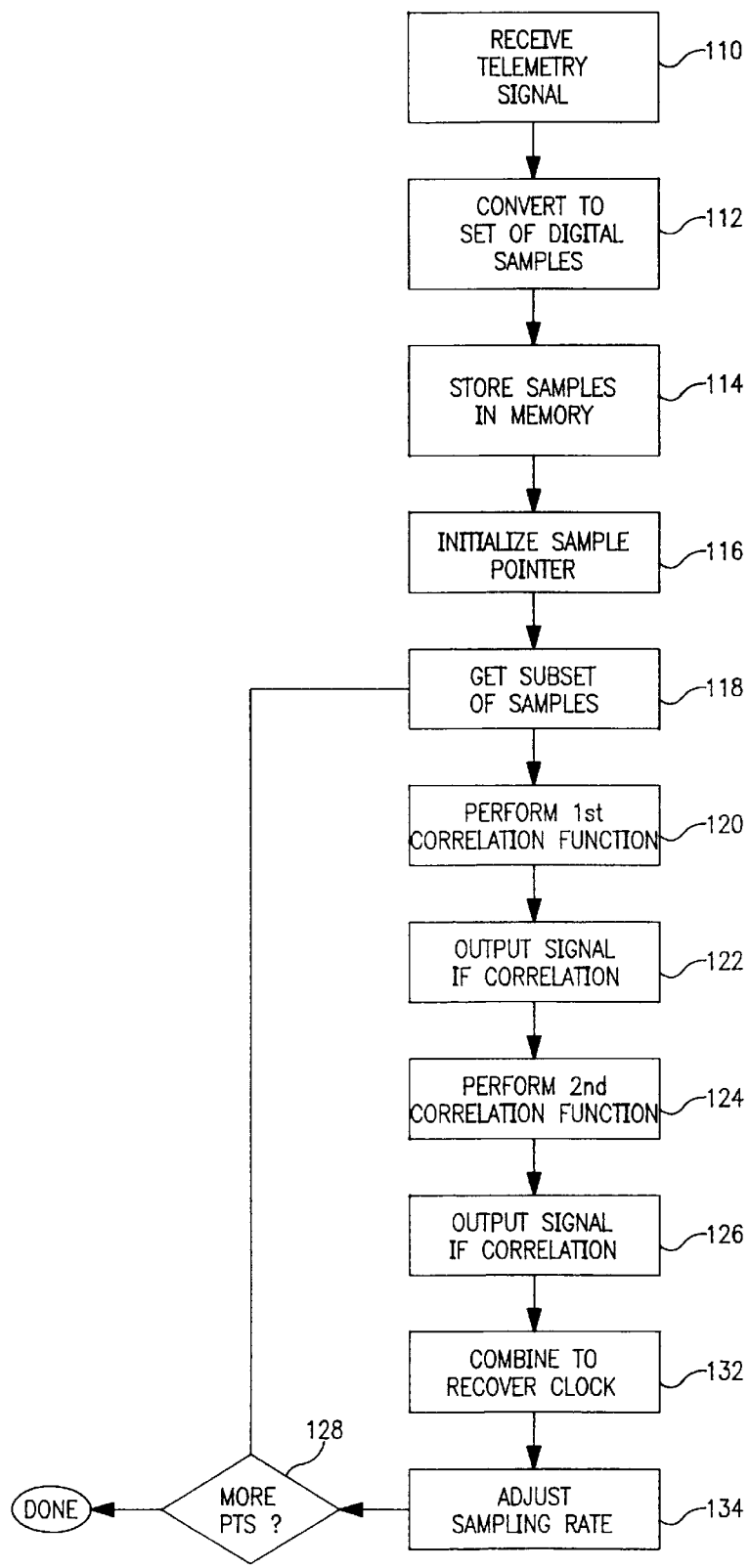
FIG. 16 is a detailed flow chart of the operation of the soft receive program of FIG. 15.

FIG. 16 presents a flow diagram of the method of demodulating the telemetry signal in conjunction with the receiver hardware depicted in FIG. 11 and the functional block diagram presented in FIG. 15. Initially at step 110, the analog telemetry signal from device 60 is received. In the present embodiment, this reception is performed by the receiving coil 72. Notably, although the present embodiment employs a coil as the receiving antenna, those skilled in the art will appreciate that the demodulation techniques disclosed herein are equally applicable to other reception means such as an RF antenna. At step 112, the analog telemetry signal is converted to a set of digital samples. In the present illustrative embodiment, the analog telemetry signal comprises a 175 kHz carrier, with seven samples representing each symbol. Accordingly, after sampling each cycle of the input comprises a set of seven samples taken at $40\mu$ second intervals. Note that the PLL shown in FIG. 11 performs the function of insuring that the seven filter samples correspond to one cycle. This sampling process continues during the entire demodulation process. As indicated at step 114, the samples are then fed to the DSP 78, which stores them in memory 79 as a set of samples representative of the incoming analog telemetry stream for processing.

Figure 17:
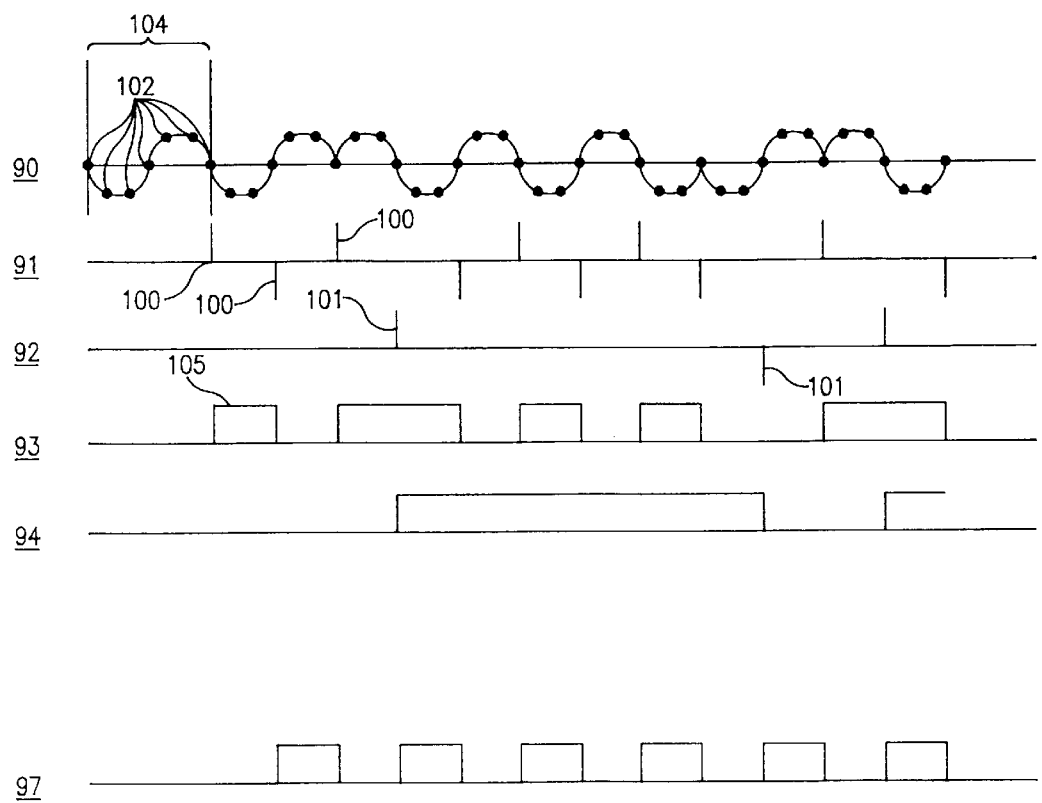
FIG. 17 depicts the signal outputs of the various components of the soft receive program of FIG. 15; and, FIG. 18A is a schematic diagram of a transmitter to be used in the external programmer, for generating selectable frequencies.

Substantially simultaneous to the reception, conversion and storage of the telemetry signal, the soft receive program 80 processes the set of samples to recover the digital data signal encoded in the original analog telemetry signal. The function of the soft receive program 80 is further understood in reference to the exemplary timing diagram of FIG. 17 along with the flow chart of FIG. 16. FIG. 17 illustrates an exemplary input signal Curve 90, which will be decoded by the soft receive program 80 to recover the clock and data signal encoded in the input signal. As indicated, Curve 90 is converted into a set of seven discrete samples 102. Of course, those skilled in the art will appreciate that any number of samples can be used to achieve a similar result, as long as the sampling rate selected is above the Nyquist rate. At step 116, a sample pointer is initialized when the demodulation process starts. The pointer is initialized to point to the first sample. As indicated at step 118, a window comprising a subset of seven samples is selected starting at the sample pointed to by the pointer. FIG. 17 illustrates the window 104 comprising a subset of seven digital data samples 102, e.g., one cycle in length over exemplary Curve 90.

As indicated at step 120, Filter A (82) correlates the convolving window 104 of samples with an expected sine wave having the carrier frequency (e.g., 175 kHz). As indicated by the example Curve 91 in FIG. 17, an output peak is produced each time a sinusoid of the carrier frequency is correlated. The output peak is positive if the sinusoid is a cosine wave and negative if the sinusoid is shifted 180°. At step 122, the output of Filter A is provided to the level detector 86, which provides a functional equivalent of a schmitt trigger, i.e., positive going peaks provide the upper trigger level and the negative going peaks provide the lower trigger level. Referring to exemplary curve 91, the level detector produces an output Curve 93. The two peaks 100 of Curve 91, for example, produce the square wave 105 of Curve 93. As a result, if the correlation is within a predefined tolerance, as determined by the level threshold, an output signal is produced.

In a similar fashion to the process performed by Filter A, Filter B (84) receives the same convolving window of seven samples as Filter A, at step 124; however, filter B performs a correlation with an absolute value sinusoid having the carrier frequency (e.g., 175 kHz). As indicated by exemplary Curve 92 of the timing diagram of FIG. 17, Filter B produces a peak when an absolute sine wave is correlated, with same polarity as the absolute sine wave. As indicated at step 126, the output of Filter B is provided to level detector 87 to provide a correlation signal within a predefined tolerance. Thus, the peaks 101 of exemplary Curve 92 produce the data output as shown at 94. As shown at 132, signals 93 and 94 are combined in logic block 88 to provide the clock output 97. At 134, the sampling rate is adjusted, as described above. Then, at 128, it is determined if there is one or more samples to process, and if so, the routine loops back to step 118.

This process of correlating continues as the window 104 moves over the entire set of samples. As indicated at step 128, 130, while more digital data samples remain the pointer is incremented and the correlation begins for the next subset. As the pointer is incremented, the window 104 moves across the samples one point at a time. As illustrated by exemplary Curve 90 of FIG. 10, the window 104 moves to the right one sample 102 each iteration through the correlation process.

Those skilled in the art will appreciate that the exemplary timing diagram of FIG. 17 is shown in an ideal form for clarity; however, in practice the input signal will contain noise. As a result, the sample data points will vary much more around the ideal sinusoid depicted in exemplary Curve 90. In such a noisy signal the output peaks, e.g.. those of Curve 91 and 92, would not be ideal peaks, but rather, would be wider and shorter. As a result, the sensitivity of the level detectors 86, 87 is adjusted accordingly to discriminate the true signal from the noise.

In addition to noise discrimination, the level detectors also provide error detection. That is, each successive peak in the Filter A and B output should have an inverted polarity with respect to each preceding peak. Accordingly, by comparing successive peaks, an error is generated if successive peaks have the same polarity.

While the process of correlating the samples continues, the outputs from level detectors 86, 87 are combined together at step 132 to recover the clock signal embedded in the telemetry signal, as seen at curve 97 of FIG. 17. Accordingly, the outputs of both level detectors 86, 87 are provided to logic function 88 which reproduces the clock signal as an output. The derived clock signal is then employed at step 134 of the flow chart of FIG. 16 to adjust the sampling rate of the A/D converter. In a preferred embodiment, the sampling rate is adjusted by providing this clock signal to a phase-locked loop 77, as shown in FIG. 11, to set the A/D sampling rate. Thus, if the sampling frequency of the receiver drifts with respect to the received carrier frequency, the phase-locked loop detects this via clock signal output 97 and adjusts the sampling rate accordingly. This results in the receiver 73 remaining locked to the signal received from transmitter 60.

Those skilled in the art will appreciate that the correlators and the level detectors of FIG. 11 can be modified to detect various encoded symbols. For example, additional correlators can be used to detect shifts in frequency, (i.e., an FSK signal). Similarly, changes can be made to the level detectors to detect changes in peaks values indicative of amplitude changes (i.e., an ASK signal).

Figure 18A:
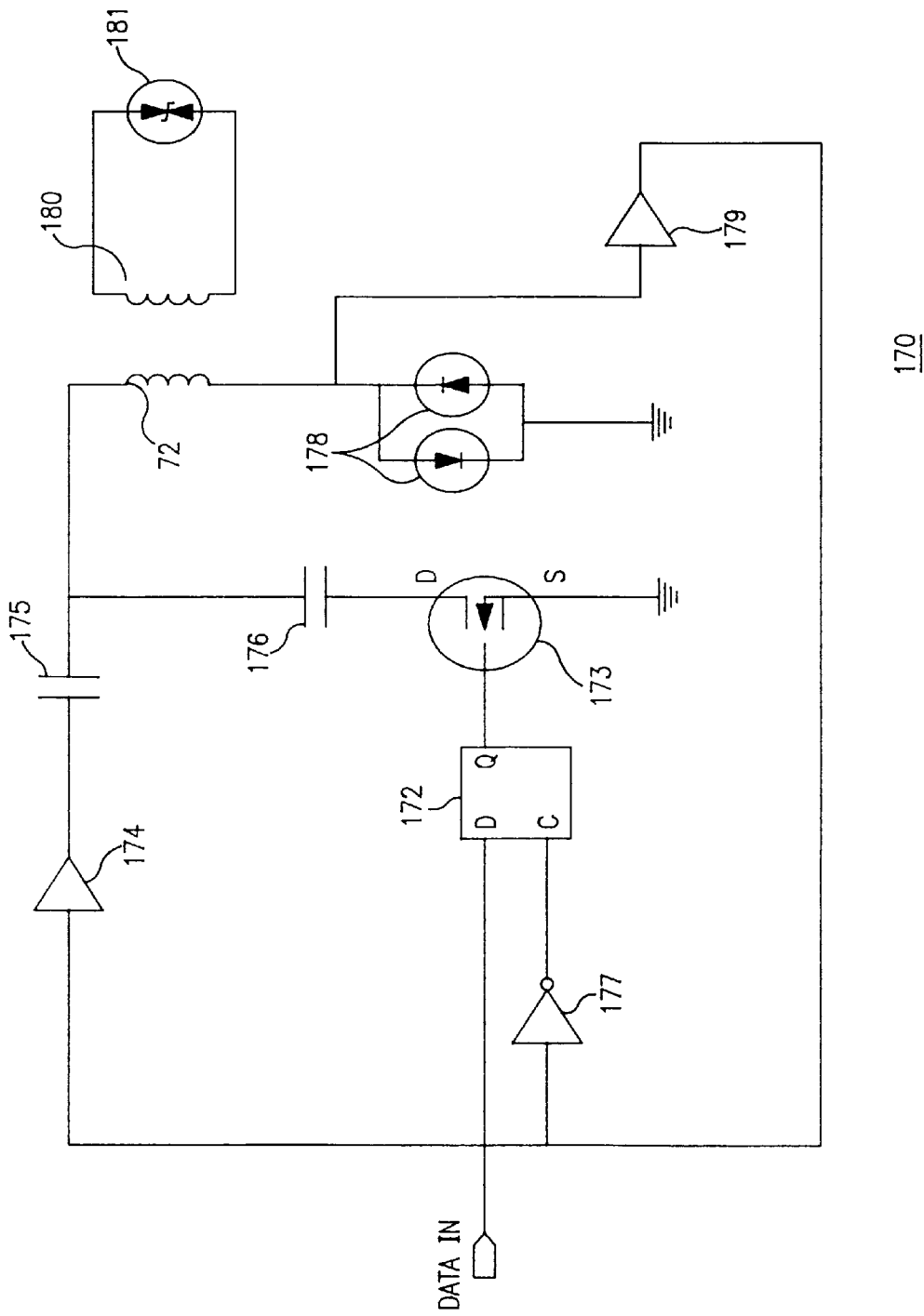
FIG. 18B depicts curves which illustrate the operation of the transmitter circuit of FIG. 18A.

Referring now to FIG. 18A, there is shown a preferred embodiment of a transmitter 170 for use an external programmer 70. In the presently preferred embodiment, the transmitter 170 transmits a digital data signal via FSK. Moreover, as with other transmitters discussed herein, the transmitter 170 employs a reflected impedance via antenna coil 72 to induce a corresponding telemetry signal in the implantable antenna coil 20. The antenna coil 72 selectively forms a tank circuit in conjunction with either capacitor 175 or both capacitors 175 and 176 to generate the telemetry signal. Thus, by selectively switching the capacitor 176 into and out of the tank circuit, the resonant frequency is altered between two frequencies. When capacitor 176 is not connected to ground through device 173, the oscillator frequency is set at the resonant frequency of coil 172 and capacitor 175 in series. The loop is closed by connecting a current sensing circuit 178, 179 to power stage 174, which cyclically provides power to the tank circuit. When capacitor 176 is switched into the circuit in parallel with a capacitor 175, the higher capacitance yields a lower frequency, thereby providing FSK encoding.

Switching is accomplished by a switching device 173, which effectively provides an FET in parallel with a diode. Device 173 is electrically coupled between the capacitor 176 and ground, and its gate is in electrical communication with the output of flip-flop 172. With device 173 connected in such a configuration, each time the output Q of flip-flop 172 is high, the FET component of device 173 is on, placing capacitor 176 in parallel with capacitor 175. On the other hand, whenever, the output Q of the flip-flop 172 is low, the FET component of device 173 is turned off, disconnecting the capacitor 176 from the resonant circuit. Frequency shifting is controlled by the data is signal to input D of flip-flop 172.

As described above with reference to the implantable transmitters, the switching of the capacitor 176 occurs at a moment of zero current through the coil 178, ensuring maximum efficiency. The moment of zero current is detected by deriving a clock signal based on current sensing techniques. To that end, an amplifier 179 is fed from the voltage measured across diodes 178. This voltage saturates the amplifier 179, generating a square wave. The generated square wave is then used to clock the flip-flop 172 via inverter 177. As a result, the flip-flop 172 can only turn on and turn off FET 173 at a moment of zero current through coil 72.

Transmitter 170 also accomplishes continuous and efficient recharging of capacitors 175, 176 during oscillator operation. This is done by also coupling the clock to capacitors 175, 176, to close the feedback loop to ensure oscillation. Since the energy bursts are delivered when the coil current is substantially zero, the voltage across capacitors 175, 176 is at a peak, minimizing the energy required to return them to a full charge. An additional inductor 180, magnetically coupled to coil 172, can be used for power monitoring and limiting purposes. An adjustable limiter 182, shown as a zener diode, is connected across 180, to control the voltage on coil 172, and thus the total magnetic field that it generates. As is known to one of skill in the art, the upward coil voltage can be determined by selection of the turns ratio between coils 172 and 180, and the zener diode.

Figure 18B:
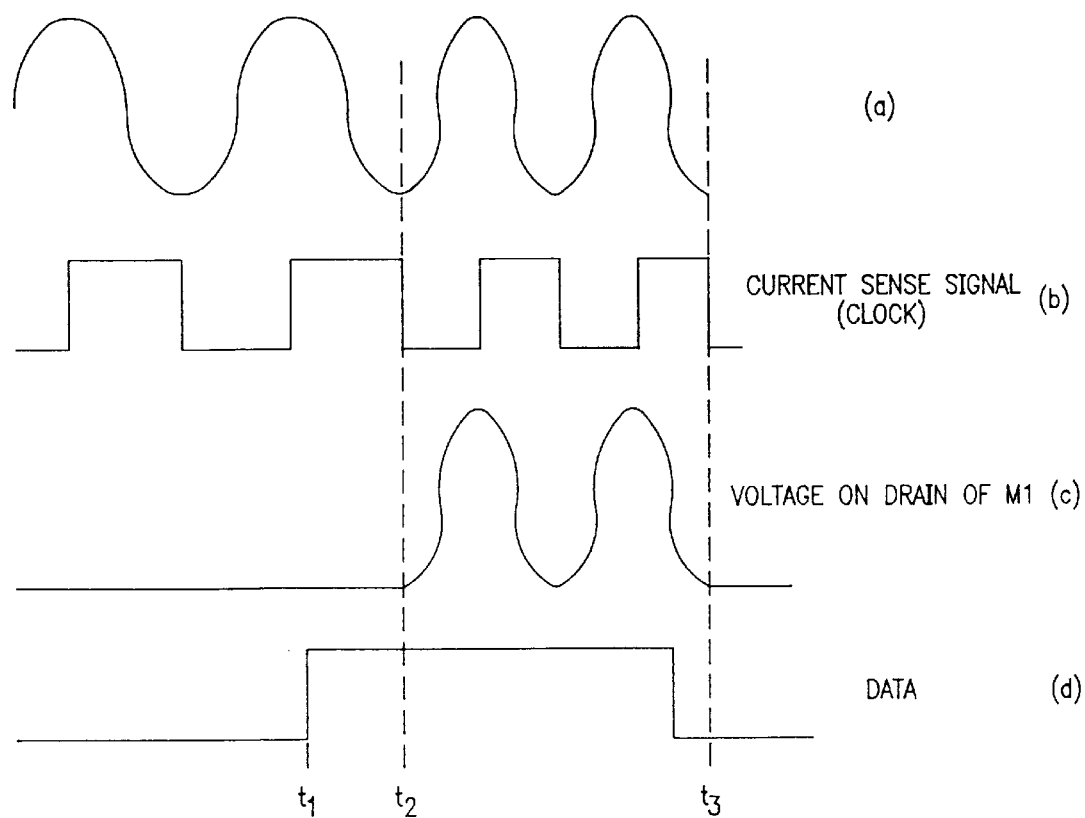

Referring now to FIG. 18B, there are shown a set of curves which illustrate further the circuit operation. Curve (a) shows the output voltage across coil 172, it being noted that the coil current lags by 90°. The current sense signal, outputted at 179, is shown in curve (b). The voltage on the drain of device 173 is shown at curve (c), and the data in signal, or the logic signal to the gate of device 173, is shown in curve (d). The data signal is initially shown as logic 0, which turns switch 173 on and holds capacitor 176 in the tank circuit. After the data signal goes high, at $t_1$, switch 173 is turned off at the next downward edge of the current sense clock signal, at $t_2$. Note that the inverter 177 produces a positive edge clock signal to flip flop 172 at time $t_2$. With the FET component of device 173 switched off, capacitor 176 is taken out of the tank circuit, and the reduced capacitance causes the frequency to shift to a higher value, as seen at curve (a).

The voltage on the drain of device 173 cannot go negative due to the effective diode between drain and source. When the data signal goes low, and device 173 is switched on again by the clock signal at $t_3$, the signal returns to its lower frequency. Note that at this time the voltage on the drain is essentially zero, as is the coil current. By switching at this time, noise is minimized, and a new symbol can be generated without any memory effects from the previous symbol. In effect, the zero current switching enables an apparent increased bandwidth, while maintaining high coil Q efficiency.

There has been disclosed an overall telemetry system and method, as well as specific component parts of the system. The system is characterized by generation of a carrier which is made up of successive sine wave symbols, each symbol being encoded in a BPSK, ASK and/or FSK format. In a preferred embodiment, the symbols are generated by switchably a tank circuit at zero crossings of the tank coil current, and the data encoding is synchronously switched, providing enhanced efficiency.

What is claimed is:

1. In an implantable device, a transmitter for generating a telemetry signal which is made up of sinusoidal symbols, comprising oscillator means for generating sinusoidal symbols, said oscillator having a high Q coil for transmitting said telemetry signal;

a source of data signals; and encoding means connected to receive said data signals, for encoding each of said symbols with a combination of BPSK, FSK and ASK data in accord with said data signals.

2. The transmitter as described in claim 1, wherein said oscillator means has means for generating successive sinusoidal symbols, and means for synchronizing generation of said symbols with said encoding.

3. The transmitter as described in claim 2, wherein said synchronizing means comprises current means for generating control signals substantially coincident with zero crossings of the current through said coil.

4. The transmitter as described in claim 3, wherein said oscillator means comprises means for generating symbols of one sinusoidal cycle.

5. The transmitter as described in claim 3, wherein said oscillator means comprises means for generating symbols of one-half sinusoidal cycle.

6. The transmitter as described in claim 3, wherein said encoding means has logic means for encoding a said symbol in accord with the data signal at the time of a said control signal.

7. The transmitter as described in claim 1, wherein said encoding means has means for encoding each said symbol with up to about 3.5 bits of data.

\* \* \* \* \*